US012723128B2

(12) United States Patent
Prouvost et al.

(10) Patent No.: US 12,723,128 B2
(45) Date of Patent: Sep. 1, 2026

(54) AROMATIC DIOL COMPOUNDS, DIEPOXIDE COMPOUNDS, POLYMERS PREPARED FROM SUCH COMPOUNDS, AND METHODS FOR MAKING THE SAME

(71) Applicant: SWIMC LLC, Cleveland, OH (US)

(72) Inventors: Benoit Prouvost, Nantes (FR); Matthieu Andriot, Attignat (FR)

(73) Assignee: SWIMC LLC, Cleveland, OH (US)

( * ) Notice: Subject to any disclaimer, the term of this patent is extended or adjusted under 35 U.S.C. 154(b) by 500 days.

(21) Appl. No.: 18/037,037

(22) PCT Filed: Nov. 15, 2021

(86) PCT No.: PCT/US2021/059403

§ 371 (c)(1),
(2) Date: May 15, 2023

(87) PCT Pub. No.: WO2022/104222

PCT Pub. Date: May 19, 2022

(65) Prior Publication Data

US 2023/0416449 A1 Dec. 28, 2023

Related U.S. Application Data

(60) Provisional application No. 63/114,150, filed on Nov. 16, 2020.

(51) Int. Cl.

| | |
|---|---|
| ***C08G 59/24*** | (2006.01) |
| ***B65D 65/42*** | (2006.01) |
| ***C07D 301/28*** | (2006.01) |
| ***C07D 303/23*** | (2006.01) |
| ***C07D 405/14*** | (2006.01) |
| ***C08G 59/26*** | (2006.01) |
| ***C08G 59/62*** | (2006.01) |
| ***C09D 163/00*** | (2006.01) |

(52) U.S. Cl.

CPC .......... *C08G 59/245* (2013.01); *B65D 65/42* (2013.01); *C07D 301/28* (2013.01); *C07D 303/23* (2013.01); *C07D 405/14* (2013.01); *C08G 59/26* (2013.01); *C08G 59/621* (2013.01); *C09D 163/00* (2013.01)

(58) Field of Classification Search

CPC .... C08G 59/24; C08G 59/245; C08G 59/246; C08G 63/193; C09D 163/00–10

See application file for complete search history.

(56) References Cited

U.S. PATENT DOCUMENTS

| | | | | |
|---|---|---|---|---|
| 3,937,685 A | | 2/1976 | Kolbel et al. | |
| 4,111,907 A | * | 9/1978 | Green | C08G 59/066 549/555 |
| 4,212,781 A | | 7/1980 | Evans et al. | |
| 4,285,847 A | | 8/1981 | Ting | |
| 4,517,322 A | | 5/1985 | Birkmeyer et al. | |
| 5,646,204 A | | 7/1997 | Akiba et al. | |
| 5,830,952 A | | 11/1998 | Pedersen et al. | |
| 7,910,170 B2 | | 3/2011 | Evans et al. | |
| 8,927,075 B2 | | 1/2015 | Gibanel et al. | |
| 9,409,219 B2 | | 8/2016 | Niederst et al. | |
| 10,000,461 B2 | | 6/2018 | Gibanel et al. | |
| 10,113,027 B2 | | 10/2018 | Niederst et al. | |
| 10,266,719 B2 | | 4/2019 | You et al. | |
| 10,501,639 B2 | | 12/2019 | O'Brien et al. | |
| 10,717,897 B2 | | 7/2020 | Gibanel et al. | |
| 2005/0089793 A1 | * | 4/2005 | Kang | C08G 59/245 430/270.1 |
| 2005/0196629 A1 | | 9/2005 | Bariatinsky et al. | |
| 2012/0296011 A1 | | 11/2012 | Kawai et al. | |
| 2022/0411679 A1 | | 12/2022 | Striewing et al. | |
| 2024/0409771 A1 | | 12/2024 | Calhoun et al. | |

FOREIGN PATENT DOCUMENTS

| | | |
|---|---|---|
| CN | 101316706 B | 1/2014 |
| CN | 105339441 B | 1/2019 |
| CN | 110337474 A | 7/2022 |
| FR | 1253177 A | 2/1961 |
| JP | H0277417 A | 3/1990 |
| JP | H09221647 A | 8/1997 |
| JP | H11140160 A | 5/1999 |
| JP | 2001-342238 A | 12/2001 |

(Continued)

OTHER PUBLICATIONS

Rao and Samui, "Phase Behavior and Photo-Responsive Studies of Photoactive Liquid Crystalline Hyperbranched Polyethers Containing Benzylidene Moiety," J. Polym. Sci. Part A: Polym. Chem 47, 2774-2786 (Year: 2009).*

Chopda et al., "Synthesis and Characterization of Epoxy methacrylate of (2E, 6E)-Bis(4-hydroxybenzylidene)-4-methycyclohexanone," J. Polym. Mater. 36(4) 391-399 (Year: 2019).*

European Search Report for EP 21892988.3 issued by the European Patent Office on Jul. 19, 2024; 16 pgs.

Database Reaxys [Online] Elsevier Life Sciences IP Limited; 2018, "Preparation of 4,4'-((adamantan-2-ylidene)methylene)diphenol", XP093184271, Database Accession No. 45906906 (Rx-ID) & Wang et al. *ACS Medicinal Chemistry Letters* 1018, 9, 803-808.

Database Reaxys [Online] Elsevier Life Sciences IP Limited; 2004, "Preparation of 1, 2, 3, 4, 8, 9, 10, 11-octafluoro-5, 7, 12, 14-tetrahydroxypentacene-6,13-dione", XP 093184278, Database Accession No. 9641165 (Rx-ID) & Sakamoto et al., *J. Am Chem .Soc*, 2004, 124, 8138-8140.

(Continued)

*Primary Examiner* — Kregg T Brooks
(74) *Attorney, Agent, or Firm* — Mueting Raasch Group

(57) ABSTRACT

A method of forming a monomer by reacting reactants including a first compound comprising an aromatic ring and a carbonyl group; a second compound comprising a carbonyl group; and optionally a third compound comprising an epoxide ring; wherein the monomer comprises a polyol (e.g., a polyphenol) or a polyepoxide. A polymer is provided that includes one or more segments derived from the monomer. The polymer may be used to prepare a coating composition, a coating, or a multi-part epoxide system. The coating composition may be applied to provide a coating on a food or beverage container.

20 Claims, 6 Drawing Sheets

(56) References Cited

FOREIGN PATENT DOCUMENTS

| | | | |
|---|---|---|---|
| JP | 2004-203951 | A | 7/2004 |
| JP | 2012-121961 | A | 6/2012 |
| JP | 2019-183107 | A | 10/2019 |
| WO | WO 03/076407 | A1 | 9/2003 |
| WO | WO 2010/140674 | A1 | 12/2010 |
| WO | WO 2011/130671 | A2 | 10/2011 |
| WO | WO 2013/119686 | A1 | 8/2013 |
| WO | WO 2015/057932 | A1 | 4/2015 |
| WO | WO 2015/179064 | A1 | 11/2015 |
| WO | WO 2017/079437 | A1 | 5/2017 |
| WO | WO 2018/125895 | A1 | 7/2018 |
| WO | WO 2019/046750 | A1 | 3/2019 |

OTHER PUBLICATIONS

Database Reaxys [Online] Elsevier Life Sciences IP Limited; 2014, "Preparation of 2, 6-bis-(4-hydroxyl-3-methoxybenzylidine)cyclohexanone", XP 093184283, Database Accession No. 554544 (Rx-ID) & Kang et al. *Monatshefte für Chemie* 2014, 145, 337-340.

Xubin et al., "Design and synthesis of dimethylaminomethyl-substituted curcumin derivatives/analogues: Potent antitumor and antioxidant activity, improved stability and aqueous solubility compared with curcumin," *Bioorg Med Chem Lett*, Jan. 9, 2013;23(5):1297-1301 (XP028976439).

Srinivasa Rao, "Molecular engineering of photoactive liquid crystalline polyester epoxies containing benzylidene moiety," *J of Polymer Science Part A: Polymer Chemistry*, Oct. 27, 2008;46(23):7637-7655.

Tampieri et al., "Microwave-assisted condensation of bio-based hydroxymethylfurfural and acetone over recyclable hydrotalcite-related materials," *Applied Catalysis B. Environmental*, Oct. 5, 2020;282(119599):1-12.

Galkin, Ananikov, "Towards Improved Biorefinery Technologies: 5-Methylfurfural as a Versatile C 6 Platform for Biofuels Development," *Chemsuschem*, Oct. 13, 2018;12(1):185-189.

International Search Report and Written Opinion for PCT/US2021/059403; issued by the Japanese Patent Office on Feb. 22, 2022; 9 pgs.

International Preliminary Report on Patentability for PCT/US2021/059403; issued by the International Bureau of WIPO, dated May 25, 2023; 7 pgs.

Third Party Observation for EP 3146009 (EP 15796095.6) from the European Patent Office, dated Aug. 6, 2018; 7 pgs.

Fache et al., "Vanillin, a promising biobased building-block for monomer synthesis," Green Chemistry, 2014;16:1987-1998.

ASTM D 5402-93, "Standard Practice for Assessing the Solvent Resistance of Organic Coatings using Solvent Rubs," Jul. 1993; 3 pgs.

ASTM D 1200-88, "Standard Test Method for Viscosity by Ford Viscosity Cup," Dec. 1988;3 pgs.

ASTM D 1652-97, "Standard Test Methods for Epoxy Content of Epoxy Resins," Oct. 1997; 2 pgs.

Shibata et al., "Fully biobased epoxy resin systems composed of a vanillin-derived epoxy resin and renewable phenolic hardeners," *European Polymer Journal*, 2017; 93:165-173.

China Patent Application No. 2021800764526, filed May 12, 2026; Office Action issued Apr. 16, 2026.

* cited by examiner

AROMATIC DIOL COMPOUNDS, DIEPOXIDE COMPOUNDS, POLYMERS PREPARED FROM SUCH COMPOUNDS, AND METHODS FOR MAKING THE SAME

CROSS REFERENCE TO RELATED APPLICATIONS

This application is the §371 U.S. National Stage of International Application No. PCT/US2021/059403, filed 15 Nov. 2021, which claims the benefit of U.S. Provisional Application No. 63/114,150, filed 16 Nov. 2020, the disclosures of which are incorporated by reference herein in their entireties.

FIELD

The present disclosure relates to aromatic diol monomers and methods for making the same. The present disclosure further relates to compositions containing the aromatic diol monomers and to polymers prepared using the aromatic diol monomers.

BACKGROUND

The application of coatings to metals to retard or inhibit corrosion is well established. This is particularly true in the area of packaging containers such as metal food and beverage cans. Coatings are typically applied to the interior of such containers to prevent the contents from contacting the metal of the container. Contact between the metal and the packaged product can lead to corrosion of the metal container, which can contaminate the packaged product. This is particularly true when the contents of the container are chemically aggressive in nature. Protective coatings are also applied to the interior of food and beverage containers to prevent corrosion in the headspace of the container between the fill line of the food product and the container lid.

Packaging coatings should preferably be capable of high-speed application to the substrate and provide the necessary properties when hardened to perform in this demanding end use. For example, the coating should be safe for food contact, not adversely affect the taste of the packaged food or beverage product, have excellent adhesion to the substrate, resist staining and other coating defects such as "popping," "blushing" and/or "blistering," and resist degradation over long periods of time, even when exposed to harsh environments. In addition, the coating should generally be capable of maintaining suitable film integrity during container fabrication and use and be capable of withstanding the processing conditions that the container may be subjected to during product packaging.

Various coatings have been used as interior protective can coatings, including polyvinyl-chloride-based coatings and epoxy-based coatings incorporating bisphenol A ("BPA"). Each of these coating types, however, has potential shortcomings. For example, the recycling of materials containing polyvinyl chloride or related halide-containing vinyl polymers can be problematic. There is also a desire by some to reduce or eliminate certain BPA-based compounds commonly used to formulate food-contact epoxy coatings.

What is needed in the marketplace is an improved binder system for use in coatings such as, for example, packaging coatings.

SUMMARY

The present disclosure relates to aromatic diol monomers, e.g., phenolic monomers, and in particular polyphenol (e.g., diphenol) monomers, epoxides thereof (e.g., diepoxides such as diglycidylethers of diphenols), and methods for making the same. The polyphenol monomers of the present disclosure include two or more phenolic groups. The present disclosure further relates to compositions containing the polyphenol monomers and to polymers prepared using the polyphenol monomers. In some embodiments, the polyphenol monomers are used in a coating composition, for example used to coat a food or beverage container.

According to an embodiment, a method of forming a monomer comprises reacting reactants including a first compound comprising an aromatic ring and a carbonyl group; a second compound comprising a carbonyl group; and optionally a third compound comprising an epoxide ring; wherein the monomer comprises a polyol (e.g., a polyphenol) or a polyepoxide. The first compound may include an alkoxide group directly attached to the aromatic ring. The first compound may include a hydroxy group, which is preferably directly attached to the aromatic ring.

According to an embodiment, the monomers of the present disclosure may be used to prepare a polymer that includes one or more segments derived from the monomer. For example, the polymer may include 5 wt-% or more, 10 wt-% or more, 20 wt-% or more, wt-% or more, 50 wt-% or more, 65 wt-% or more, 80 wt-% or more, 90 wt-% or more, or wt-% or more, or 99 wt-% or more; and/or 100 wt-% or less, 95 wt-% or less, 90 wt-% or less, 80 wt-% or less, 60 wt-% or less, 40 wt-% or less, 20 wt-% or less, or 10 wt-% or less of structural units derived from monomers.

The polymer may be used to prepare a coating composition, a coating, or a multi-part epoxide system. The coating composition may be applied to provide a coating on a food or beverage container.

DEFINITIONS

Figure 1A:
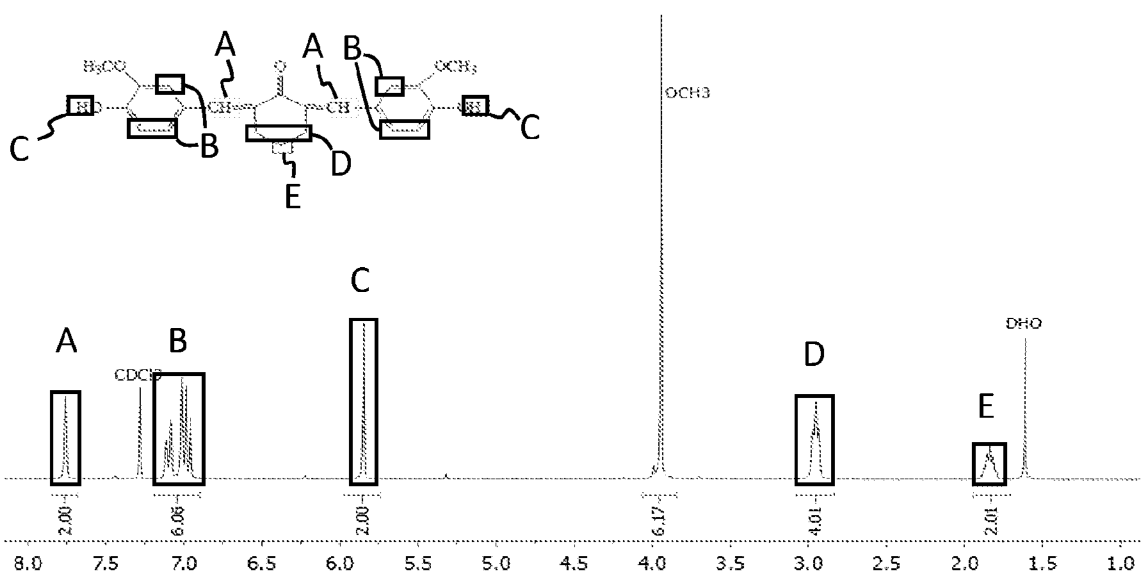
FIG. 1A is an NMR spectrum of the compound prepared in Example 1A.

The term "oligomer" is used here to refer to a compound including from 2 to 10 (inclusive) repeating units (monomers). Each repeating unit may have a limited molecular weight, such as 100 or less, 200 or less, 500 or less, or 1000 or less. The oligomer may have a limited molecular weight, such as 1000 or less, 1500 or less, or 2000 or less.

Unless otherwise indicated, the terms "polymer" and "polymeric material" include, but are not limited to, organic homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic, and atactic symmetries.

The term "aromatic ring" is used in this disclosure to refer to a conjugated ring system of an organic compound. Aromatic rings may include carbon atoms only, or may include one or more heteroatoms, such as oxygen, nitrogen, or sulfur.

The term "organic group" is used here to refer to a hydrocarbon group (with optional elements other than carbon and hydrogen, such as oxygen, nitrogen, phosphorus, sulfur, and silicon) that may be further classified as an aliphatic group, cyclic group (e.g., aromatic and cycloaliphatic groups), or combination of aliphatic and cyclic groups (e.g., alkaryl and aralkyl groups).

The term "aliphatic group" is used here to refer to a saturated or unsaturated linear or branched hydrocarbon group. This term is used to encompass alkyl, alkenyl, and alkynyl groups, for example.

The term "alkylated" is used in this disclosure to describe compounds that are reacted to replace a hydrogen atom or a negative charge of the compound with an alkyl group, such that the alkyl group is covalently bonded to the compound.

The term "alkyl" is used in this disclosure to describe a monovalent group that is a radical of an alkane and includes straight-chain, branched, cyclic, and bicyclic alkyl groups, and combinations thereof, including both unsubstituted and substituted alkyl groups. Unless otherwise indicated, the alkyl groups typically contain from 1 to 30 carbon atoms. In some embodiments, the alkyl groups contain 1 to 20 carbon atoms, 1 to 10 carbon atoms, 1 to 6 carbon atoms, 1 to 4 carbon atoms, or 1 to 3 carbon atoms. Examples of alkyl groups include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, etc.

The term "hetero atom" is used here to refer to an atom other than carbon or hydrogen. Examples of hetero atoms include N, P, S, O, and the like.

The term "cyclic group" means a closed ring hydrocarbon group that is classified as an alicyclic group or an aromatic group, both of which can include heteroatoms.

The term "phenol" is used here to refer to an aromatic hydrocarbon compound having one or more hydroxyl groups directly bonded to a carbon atom of the aromatic ring (typically a six-carbon aromatic ring).

The term "polyphenol" is used here to refer to a polyhydric material having two or more phenylene groups that each include a hydroxyl group attached to a carbon atom of the ring. The term "diphenol" refers to a polyphenol in which two phenylene groups each have one hydroxyl group.

The term "phenylene" as used herein refers to a six-carbon atom aromatic ring (e.g., as in a benzene group) that can have any substituent groups (including, e.g., hydrogen atoms, halogens, hydrocarbon groups, oxygen atoms, hydroxyl groups, etc.). Thus, for example, the following aromatic groups are each phenylene rings: $—C_6H_4—$, $—C_6H_3(CH_3)—$, and $—C_6H(CH_3)_2Cl—$. In addition, for example, each of the aromatic rings of a naphthalene group are phenylene rings.

The term "bisphenol" refers to a polyhydric polyphenol having two phenylene groups that each include a six-carbon ring and a hydroxyl group attached to a carbon atom of the ring, wherein the rings of the two phenylene groups do not share any atoms in common.

The term "crosslinker" refers to a molecule capable of forming a covalent linkage between separate polymers or between two different regions of the same polymer.

The terms "estrogenic activity" or "estrogenic agonist activity" refer to the ability of a compound to mimic hormone-like activity through interaction with an endogenous estrogen receptor, typically an endogenous human estrogen receptor.

The term "group" is intended to be a recitation of both the particular moiety, as well as a recitation of the broader class of substituted and unsubstituted structures that includes the moiety. Thus, when the term "group" is used to describe a chemical substituent, the described chemical material includes the unsubstituted group (e.g., the moiety) and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, isopropyl, t-butyl, heptyl, dodecyl, octadecyl, amyl, 2-ethylhexyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, isopropyl, t-butyl, heptyl, dodecyl, octadecyl, amyl, 2-ethylhexyl, and the like.

The term "reactive" is used here to mean that a reaction between the intended compounds takes place in the desired processing conditions within a reasonable amount of time, such as a yield of 50% or more, 75% or more, or 90% or more is reached within 12 hours or less, 4 hours or less, 2 hours or less, or 1 hour or less.

The term "substantially" as used here has the same meaning as "significantly," and can be understood to modify the term that follows by at least about 90%, at least about %, or at least about 98%. The term "substantially free" of a particular compound means that the compositions of the present invention contain less than 1,000 parts per million (ppm) of the recited compound (corresponding to less than 0.1 wt. %). The term "essentially free" of a particular compound means that the compositions of the present invention contain less than 100 parts per million (ppm) of the recited compound. The term "completely free" of a particular compound means that the compositions of the present invention contain less than parts per billion (ppb) of the recited compound. In the context of the aforementioned phrases, the compositions of the present invention contain less than the aforementioned amount of the compound whether the compound itself is present in unreacted form or has been reacted with one or more other materials. As will be appreciated by persons having ordinary skill in the art, the amount of a compound in an ingredient, polymer, formulation, or other component typically may be calculated based on the amounts of starting materials employed and yields obtained when making such ingredient, polymer, formulation, or other component.

The term "not substantially" as used here has the same meaning as "not significantly," and can be understood to have the inverse meaning of "substantially," i.e., modifying the term that follows by not more than 25%, not more than 10%, not more than 5%, or not more than 2%.

The term "about" is used here in conjunction with numeric values to include normal variations in measurements as expected by persons skilled in the art, and is understood have the same meaning as "approximately" and to cover a typical margin of error, such as ±5% of the stated value.

Terms such as "a," "an," and "the" are not intended to refer to only a singular entity, but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination of any two or more of the listed elements.

The recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" or "at least" a particular value, that value is included within the range.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

DETAILED DESCRIPTION

The present disclosure broadly relates to polymerizable monomers. In particular, the present disclosure relates to aromatic diol monomers, such as polyphenol monomers (e.g., diphenol), to polyepoxide monomers, and methods for making the same. The aromatic diol (e.g., diphenol) monomers of the present disclosure may be used as alternatives to bisphenols (e.g., bisphenol A). Similarly, the polyepoxide monomers may be use as alternatives to epoxides of bisphenols (e.g., the diglycidyl ether of bisphenol A also commonly known as BADGE).

The present disclosure further relates to compositions containing the aromatic diol (e.g., polyphenol) monomers and/or the polyepoxide monomers and to polymers prepared using one or both of the aromatic diol (e.g., polyphenol) monomers and the polyepoxide monomers. In some embodiments, the monomers are used (e.g., as structural units of a polymer) in a coating composition. In some embodiments, the monomers are used (e.g., as structural units of a polymer) in a can coating composition. In some embodiments, the monomer (e.g., a diepoxide monomer derived from a diphenol monomer) is used in a thermoset coating composition. The monomers may also be used in other thermoset compositions such as, for example, composites.

According to an embodiment, aromatic diol (e.g., polyphenol, such as diphenol) monomers may be prepared from a first compound having an aromatic ring and a carbonyl group and a second compound having a carbonyl group. Such monomers may be prepared by a method that includes reacting the first compound and the second compound. The method may optionally include reacting with a third compound having an epoxide ring. The monomer may be an aromatic diol, a polyphenol, or a polyepoxide. For example, the monomer may be a diphenol or a diepoxide derived from the diphenol.

According to an embodiment, the first compound includes an alkoxide group directly attached to the aromatic ring. The first compound may include a hydroxy group, which is preferably directly attached to the aromatic ring. The carbonyl group of the first compound may be an acyl group, preferably —CH(═O) or an acetyl group. The carbonyl group (e.g., the acyl group, —CH(═O), or acetyl group) is preferably directly attached to the aromatic ring.

In some embodiments, the first compound is represented by Formula (I):

Formula (I)

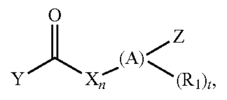

wherein A is an aromatic ring, optionally substituted and optionally including a hetero atom, wherein the hetero atom is preferably O, N, or S;

wherein each $R_1$ and Y are independently hydrogen or an organic group (e.g., an aliphatic group, a cycloaliphatic group, or an aromatic group);

wherein X is an organic group (e.g., a $C_1$-$C_{20}$, $C_1$-$C_{10}$, or $C_1$-$C_4$-containing group such as an aliphatic group, a cycloaliphatic group, an aromatic group) or is absent (when n is 0);

wherein Z is a group reactive with epichlorohydrin (e.g., a hydroxyl group or hydroxy-containing group including one or more carbon atoms, or a primary or secondary amino group);

wherein n is 0 or 1;

wherein t is 2 to 4.

In one embodiment, n in Formula (I) is zero (0) and the carbonyl-bearing carbon is directly attached to the aromatic ring.

In one embodiment Y is a hydrogen and the first compound is represented by Formula (IA):

Formula (IA)

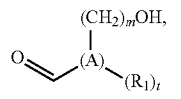

wherein A, $R_1$, and t are as in Formula (I), preferably wherein $R_1$ is hydrogen or an aliphatic group comprising oxygen; and wherein m is 0 to 2.

The first compound may have an atomic weight of less than 1,000 Daltons, less than 500 Daltons, or less than 200 Daltons. In some embodiments the first compound is an oligomer with a repeating unit having an atomic weight of less than 1,000 Daltons.

In some embodiments, the first compound is vanillin, hydroxymethyl furfural, a hydroxybenzaldehyde (e.g., 4-hydroxybenzaldehyde or 2-hydroxybenzaldehyde), a hydroxyl naphthaldehyde (e.g., 1-hydroxy-2-naphthaldehyde, 3-hydroxy-2-naphthaldehyde, or 4-hydroxy-1-naphthaldehyde), 3-hydroxyacetophenone, a substituted variant thereof, or a combination thereof. In a preferred embodiment, the first compound is vanillin or hydroxymethyl furfural ("HMF").

In some embodiments, the second compound is represented by Formula (II):

Formula (II)

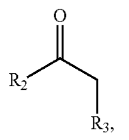

wherein $R_2$ and $R_3$ are each independently hydrogen or an organic group. For example, $R_2$ and $R_3$ may be independently selected from a $C_1$-$C_{20}$, $C_1$-$C_{10}$, or $C_1$-$C_4$-containing group such as an aliphatic group, a cycloaliphatic group, or an aromatic group. $R_2$ and $R_3$ may optionally be fused in a ring, such as a five-member or six-member ring (e.g., a cyclohexane ring).

In some embodiments, the second compound is cyclohexanone, a dialkyl ketone (preferably diethyl ketone or acetone), an alkyl dione (preferably cyclohexanedione), levulinic acid, a substituted variant thereof (e.g., cyclohexanone with one or more hydrogen atoms replaced with a substituent group such as a carbon-containing group), or a combination thereof.

The second compound may have an atomic weight of less than 1,000 Daltons, less than 500 Daltons, or less than 100 Daltons. In some embodiments the second compound is an oligomer with a repeating unit having an atomic weight of less than 1,000 Daltons.

In some embodiments the method includes reacting the first compound or an intermediate product of the first and second compounds with the third compound. The third compound may be an epihalohydrin, preferably epichlorohydrin.

The method may include reacting the first compound with the second compound in a first step resulting in an intermediate product (e.g., an aromatic diol such as a polyphenol, preferably a diphenol) and then reacting the intermediate product with the third compound in a second step resulting in the monomer. For example, the method may include first creating a diphenyl and then adding an epoxide group to the diphenyl. The monomer may be a polyepoxide monomer, preferably a diepoxide monomer. In some embodiments, the method only includes the first step of reacting the first compound with the second compound, and the monomer is the reaction product of the first step (e.g., an aromatic diol such as a polyphenol, preferably a diphenol).

Alternatively, the method may include reacting the first compound and the third compound in a first step resulting in an intermediate product and reacting the intermediate product with the second compound in a second step resulting in the monomer. For example, the method may include first creating an epoxide functional phenyl compound and then reacting the epoxide functional phenyl compound with a carbonyl-containing compound to create an epoxide functional diphenyl. The monomer may be a polyepoxide monomer, preferably a diepoxide monomer.

Suitable epihalohydrins that can be used in the methods of the present disclosure include those represented by the following formula:

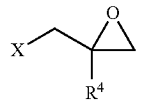

where $R^4$ is hydrogen or a hydrocarbyl group having from 1 to 4 carbon atoms, preferably hydrogen; and X is a halogen, preferably chlorine or bromine, most preferably chlorine. Epichlorohydrin is a preferred epihalohydrin for use in the methods of the present disclosure.

According to an embodiment, the first compound and the second compound are reacted at a ratio of about 2 mol parts of the first compound to about 1 mol part of the second compound. For example, the first compound and the second compound may be reacted at a ratio from 1.8:1 to 3:1 mole parts, from 1.8:1 to 2.5:1 mole parts, from 1.8:1 to 2.2:1 mole parts, or from 2:1 to 2.2:1 mole parts of the first compound and the second compound. In a preferred embodiment, the ratio of the first compound to the second compound is 2:1 or approximately 2:1 (e.g., from 2:1 to 2.2:1) to minimize incomplete reactions that could result in the formation of monofunctional monomers rather than difunctional (e.g., diphenyl) monomers.

According to an embodiment, the method may be used to synthesize a monomer of Formula (III):

Formula (III)

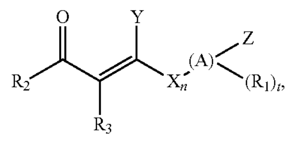

wherein A, $R_1$, X, Y, Z, n, and t are as in Formula (I) and $R_2$ and $R_3$ are as in Formula (II).

The monomer may be a diphenol. According to an embodiment, the monomer is represented by Formula (IIIA):

Formula (IIIA)

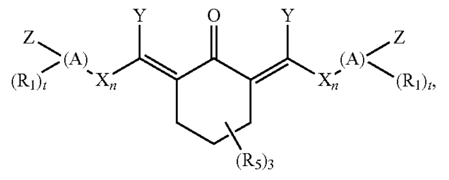

wherein A, $R_1$, X, Y, Z, n, and t are as in Formula (I), each $R_5$ is independently selected from hydrogen or an organic group, preferably where $R_5$ is hydrogen. For example, when the method includes reacting the first compound with cyclohexanone as the second compound, the resulting monomer may be of Formula (IIIA).

According to an embodiment, the monomer is represented by Formula (BIB):

Formula (IIIB)

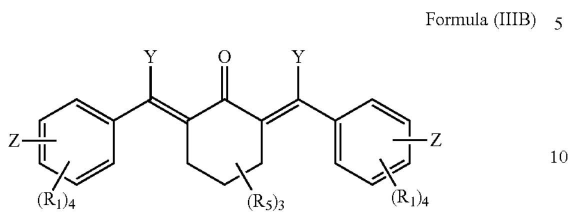

wherein $R_1$, Y, and Z are as in Formula (I) and $R_5$ is as in Formula (IIIA). For example, when the method includes reacting a first compound that has a substituted benzene ring with cyclohexanone as the second compound, the resulting monomer may be of Formula (IIIB).

According to an embodiment, the monomer is represented by Formula (IIIC):

Formula (IIIC)

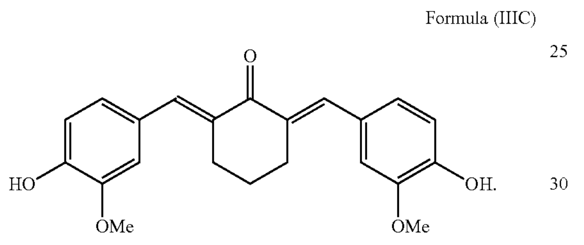

For example, when the method includes reacting vanillin as the first compound with cyclohexanone as the second compound, the resulting monomer may be of Formula (IIIC).

According to an embodiment, the monomer is represented by Formula (IIID):

Formula (IIID)

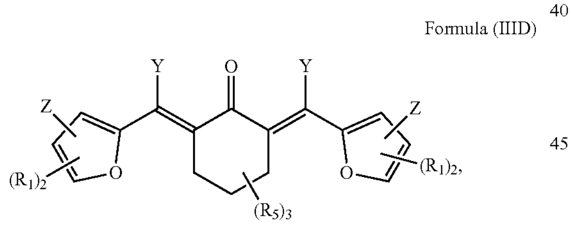

wherein $R_1$, Y, and Z are as in Formula (I) and $R_5$ is as in Formula (IIIA). For example, when the method includes reacting a first compound that has a substituted furan ring with cyclohexanone as the second compound, the resulting monomer may be of Formula (IIID).

According to an embodiment, the monomer is represented by Formula (IIIE)

Formula (IIIE)

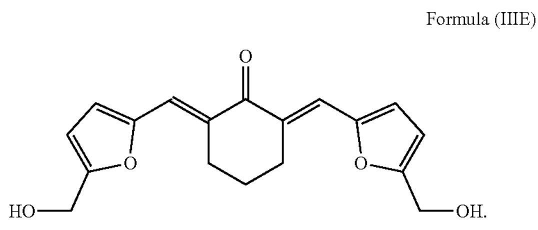 [SMILES: O=C1/C(=C/c2ccc(CO)o2)CCC/C1=C\c1ccc(CO)o1]

For example, when the method includes reacting HMF as the first compound with cyclohexanone as the second compound, the resulting monomer may be of Formula (IIIE).

According to an embodiment, the depicted Z groups (group reactive with epichlorohydrin) may be converted to epoxide-containing groups such that the monomer is an epoxide, preferably a diepoxide. For example, the method may include reacting the compound of Formula (III) with a third compound, where the third compound is an epoxide-functional compound, such as an epihalohydrin, preferably epichlorohydrin.

According to an embodiment, the monomer is represented by Formula (IV):

Formula (IV)

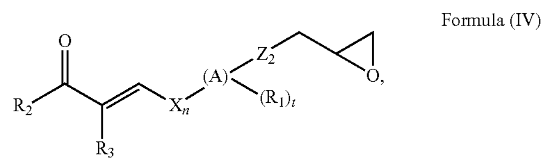

wherein A, $R_1$, X, Y, n, and t are as in Formula (I) and $R_2$ and $R_3$ are as in Formula (II), and wherein $Z_2$ is a residue of Z after reaction with epichlorohydrin, preferably wherein $Z_2$ is oxygen, —NH—, —$(CH_2)_mO$— where m is 1 or 2, or —COO—.

According to an embodiment, the monomer is represented by Formula (IVA):

Formula (IVA)

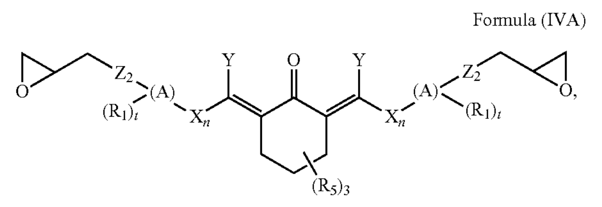

wherein A, $R_1$, X, Y, n, and t are as in Formula (I), $R_5$ is as in Formula (IIIA), and wherein $Z_2$ is as in Formula (IV).

According to an embodiment, the monomer is represented by Formula (IVB):

Formula (IVB)

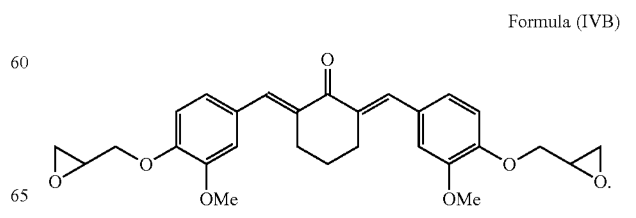

According to an embodiment, the monomer is represented by Formula (IVC):

Formula (IVC)

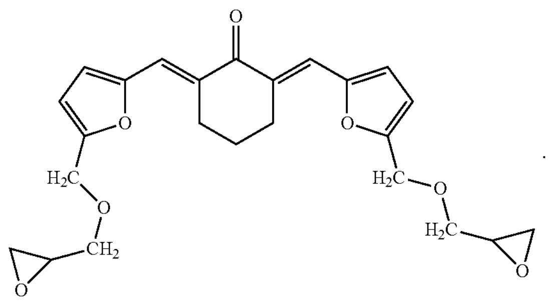

According to an embodiment, the monomer is represented by Formula (IVD):

Formula (IVD)

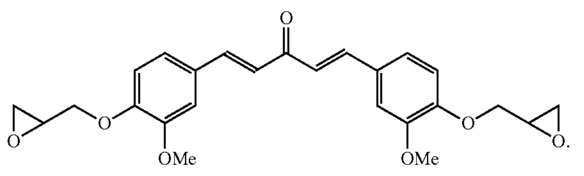

In some embodiments, reacting the first compound or an intermediate product of the first and second compounds with the third compound is done in the presence of a phase transfer catalyst. Examples of suitable phase transfer catalysts include various quaternary ammonium salts and quaternary phosphonium salts. Any suitable ammonium or phosphonium salt may be used. One example of a suitable ammonium salt is benzyl triethyl ammonium chloride ("TEBAC").

Reacting the first compound or an intermediate product of the first and second compounds with the third compound may include combining 1 mol part of the first compound or its residue with 1 mol part or more of the third compound. If the intermediate product of the first and second compounds includes two residues of the first compound (e.g., is a diphenyl), each residue accounts for a mole equivalent. In some embodiments, the third compound (e.g., epihalohydrin) is provided in excess. The method may include combining 1 mol part of the first compound with 2 mol parts or more, 3 mol parts or more, 4 mol parts or more, or preferably 5 mol parts or more of epihalohydrin. The method may include combining 1 mol part of the first compound with 20 mol part or less, 15 mol parts or less, 10 mol parts or less, or 8 mol parts or less of epihalohydrin. The method may include combining 1 mol part of the first compound with 1 to 20 mol parts, 2 to 15 mol parts, or 3 to 10 mol parts of epihalohydrin. In one exemplary embodiment, 1 mol part of the first compound is combined with about 5 mol parts of epihalohydrin.

Reacting the first compound or an intermediate product of the first and second compounds with the third compound (e.g., epihalohydrin) in the presence of the phase transfer catalyst may include combining 1 mol part of the third compound with 1/1000 mol part or more, 1/100 mol part or more, 1/50 mol part or more, 1/20 mol part or more, or preferably 1/10 mol part or more of the phase transfer catalyst. The method may include combining 1 mol part of the third compound with ½ mol part or less or preferably ⅕ mol parts or less of the phase transfer catalyst. In one exemplary embodiment, 1 mol part of the third compound is combined with 1/50 to 1/150 mol part of the phase transfer catalyst. As previously discussed, in preferred embodiments, the phase transfer catalyst may be a quaternary ammonium salt or a quaternary phosphonium salt, preferably a quaternary ammonium salt.

The percent yield of the reaction is based on the amount of the target compound (e.g., monomer, oligomer, or polymer) actually achieved, by weight, as compared to a theoretical maximum yield of the reaction.

If desired, one or more diluents or other materials may be present in the reaction mixture. For example, organic solvent may be included in the reaction mixture. The amount and identity of such diluents or other materials are preferably controlled to avoid unsuitable interfering with the desired reaction or with downstream reactions, including polymerization reactions, that may be used to form further products or polymers from reaction products, such as the first intermediate product. In some embodiments, the pH of the reaction mixture is lowered with an acid or increased with a base. For example, the pH of the reaction mixture of vanillin and cyclohexanone may be lowered with an acid (e.g., HCl). The pH of the reaction mixture of vanillin epoxide and acetone may be increased with a base (e.g., NaOH).

The monomers of the present disclosure (e.g., monomers of Formula (III) or Formula (IV)) may have any suitable molecular weight. The monomers may have a number average molecular weight (Mn) of up to about 3,000, up to about 2,000, up to about 1,200, up to about 800, up to about 600, or up to about 500 Daltons as evaluated, for example, using gel permeation chromatography and a polystyrene standard.

In embodiments where the monomer is a polyepoxide, the monomer may also be characterized based on its epoxy equivalent weight. Epoxy equivalent weight may be determined, for example, by titration with perchloric acid. In some embodiments, the monomer has an epoxy equivalent weight of 200 or greater (e.g., 206), 210 or greater (e.g., 219), or 230 or greater (e.g., 243). In some embodiments, if vanillin is used as the first compound, the monomer may have an epoxy equivalent weight of 210 or greater or 230 or greater, and up to 250 (e.g., if cyclohexanone is used as the second compound and epichlorohydrin is used as the halohydrin).

The method may include various washing, drying, extraction, and/or filtration steps. For example, the method may include removing excess epihalohydrin. Excess epihalohydrin may be removed, for example, by distillation (such as vacuum distillation). After excess epihalohydrin is removed, less than 1 wt-% of epihalohydrin may remain in the reaction mixture. The method may also include washing the monomer. According to preferred embodiments, less than 1000 ppm, less than 500 ppm, less than 100 ppm, less than 50 ppm, less than 25 ppm, or less than 10 ppm of epihalohydrin remains in the final monomer composition or the final polymer composition after forming of the monomer. The unit "ppm" (parts per million) is used here to refer to the amount by weight.

The monomers of the present disclosure may have utility in a variety of different end uses. The monomers may form part of a polymerizable composition. Such polymerizable compositions may take multiple forms and be used, for example, to synthesize polymers for use in formulating liquid or powder coating compositions for use in coating a variety of substrates, but especially metal substrates such as industrial coil and metal substrates for use in forming packaging articles such as food and beverage containers (e.g., cans) or portions thereof. Other coating end uses may include industrial coatings, marine coatings (e.g., for ship hulls), coatings for storage tanks (e.g., metal or concrete), architectural coatings (e.g., on cladding, metal roofing, ceilings, garage doors, etc.), coatings for gardening tools and equipment, toy coatings, automotive coatings, metal furniture coatings, coil coatings for household appliances, floor coatings, and the like.

In preferred embodiments, the coating composition is suitable for use as an adherent packaging coating and, more preferably, as an adherent coating on an interior and/or exterior surface of a food or beverage container. Thus, in preferred embodiments, the coating composition is suitable for use as a food-contact coating. It is also contemplated that the coating composition may have utility in cosmetic packaging or medical packaging coating end uses, and as a drug-contact coating in particular (e.g., as an interior coating of a metered dose inhaler can—commonly referred to as an "MDI" container). It is also contemplated that the coating composition may have utility in coating applications in which the coated substrate will contact bodily fluids such as, e.g., as an interior coating of a blood vial.

As discussed in detail later herein, the polymers disclosed herein are formed from ingredients that include an aromatic diol compound, such as a polyphenol (e.g., diphenol) compound. Any suitable aromatic diol (e.g., polyphenol) compound or combination of aromatic diol compounds may be employed, with diphenol compounds being preferred in certain embodiments.

The polymer may have any suitable backbone chemistry and may be a linear or branched polymer. In preferred embodiments, however, the polymer is a linear or substantially linear polymer. Typically, the backbone will include one or more heteroatoms (e.g., O, N, or S), and more typically a plurality of heteroatoms.

It is contemplated that the monomers of the present disclosure may be used to make any type of polymer in which polyepoxide or polyphenol reactants are typically used, including, for example, polymers for use in the coatings or adhesives industries. The monomers disclosed herein are particularly useful for use in making binder polymers (e.g., polyethers, polyesters, copolymers thereof, and the like) for use in the coating industry, including the types of polyester and polyether binder polymers used to formulate coating compositions intended for use on the interior or exterior surfaces of food or beverage containers (e.g., metal food or beverage cans or portions thereof). One or both of the polyphenol and polyepoxide monomers of the present disclosure may be use to prepare binder polymers suitable for use in liquid, powder, laminate, or extrusion coating compositions in which the coating composition, as applied to the substrate to be coated, preferably includes the preformed polymer. A preformed polymer in this context means that the polymer in the coating composition has a number average molecular weight of 2000 or greater, 3000 or greater, 3500 or greater, or 4000 or greater. The number average molecular weight of the polymer may have any suitable upper limit, such as up to 100,000, up to 50,000, up to 20,000, or up to 10,000.

In certain preferred embodiments, the polymer is a polyether polymer that preferably includes a plurality of ether linkages in its backbone. If desired, the backbone of the polymer may include linkages having one or more heteroatoms (e.g., step-growth or condensation linkages) other than ether linkages (e.g., in addition to, or in place of, the ether linkages) such as, for example, amide linkages, carbonate linkages, ester linkages, urea linkages, urethane linkages, or sulfur-containing linkage (e.g., carbon-sulfur chain linkages) and the like, or combinations thereof. Thus, for example, in some embodiments, the backbone may include both ester and ether linkages. In some embodiments, the polymer is a polyether polymer that is free of backbone condensation linkages or step-growth linkages other than ether linkages. In one embodiment, the polymer is free of backbone ester linkages.

The polymer includes aromatic groups. Preferably, the polymer includes a plurality of aromatic groups attached to the backbone. The backbone of the polymer may include any suitable terminal groups, including, for example, one or more phenolic groups, one or more oxirane groups, or both phenolic and oxirane groups.

While not intending to be bound by any theory, it is believed that the inclusion of a sufficient number of aryl and/or heteroaryl groups (typically phenylene groups) in the polymer is an important factor for achieving suitable coating performance for food-contact packaging coatings, especially when the product to be packaged is a so called "hard-to-hold" food or beverage product. Sauerkraut is an example of a hard-to-hold product. In preferred embodiments, aryl and/or heteroaryl groups constitute at least about 10 weight percent ("wt-%"), more preferably at least about 25 wt-%, and even more preferably at least about 35 wt-% or at least about 45 wt-% of the polymer, based on the total weight of aryl and heteroaryl groups in the polymer relative to the weight of the polymer. The upper concentration of aryl/heteroaryl groups is not particularly limited, but preferably the amount of such groups is configured such that the Tg of the polymer is within the Tg ranges previously discussed. The total amount of aryl and/or heteroaryl groups in the polymer will typically constitute less than about 80 wt-%, more typically less than about 75 wt-%, and even more typically less than about 70 wt-% or less than about 60 wt-% of the polymer. The total amount of aryl and/or heteroaryl groups in the polymer can be determined based on the weight of aryl- or heteroaryl-containing monomer incorporated into the polymer and the weight fraction of such monomer(s) that constitutes aryl or heteroaryl groups.

The monomers of the present disclosure may form part of a multi-part thermoset composition such as, for example, one in which two or more parts are brought together to form a final composition (e.g., a final thermoset composition) immediately or shortly prior to use. A multi-part epoxide system may include a first part (e.g., part A) comprising the polyepoxide monomer of the present disclosure; and a second part (e.g., part B) comprising a hardener. Suitable hardeners include, for example, polyamines and polyamidoamines. Such multi-part epoxide compositions may be used for a variety of purposes, including, for example, castings, adhesives, fillers, and certain coating applications. For example, the multi-part epoxide compositions may be used to coat interior surfaces of concrete or metal tanks that may hold a variety of products, including liquid products for human consumption such as potable water, edible syrups and oils (e.g., corn syrup), other liquid feedstocks, and the like. Examples of such multi-part epoxide compositions, including suitable hardener or second parts for use with the first part of the present disclosure are disclosed in U.S. Prov. Appl. No. 62/938,541 filed on Nov. 21, 2019.

The diphenol monomers may be used as a cross-linker and/or as part of a copolymer composition. For example, the polyphenol monomer may be a precursor to crosslinking monomers (e.g., oxirane functional methacrylate) or may be a crosslinking agent (e.g., with a polycyclocarbonate functional polymer or a polyepoxide).

In some embodiments, a polyphenol, typically a diphenol, or mixture of polyphenols is upgraded with a polyepoxide, typically a diepoxide, or mixture of polyepoxides, to build molecular weight and produce a polyether polymer having the desired molecular weight and balance of other desired characteristics. In such embodiments, one or both of one or more polyphenols and one or more polyepoxides are monomers of the present disclosure (e.g., monomers of Formulas (III) or (IV)). A polycyclocarbonate, typically a dicyclocarbonate, may be used in place of a polyepoxide to upgrade a diphenol of the present invention to form a polyether polymer. Examples of such polycyclocarbonate materials for use in reacting with polyphenols to form polyether polymers are provided in U.S. Pat. Nos. 10,000,461 and 10,717,897. For example, the polycyclocarbonate material may include dicyclocarbonates selected from diglyceroldicyclocarbonate, (glycerolcyclocarbonate) dicarbonate, or a combination thereof. In embodiments where the polyphenol (e.g., diphenol) is reacted with a polycyclocarbonate (e.g., dicyclocarbonate), the resulting polyether may be free of epoxide groups.

In other embodiments, a polyepoxide of the present disclosure, typically a diepoxide, is upgraded with one or more extenders other than, or in addition to, a polyphenol. Examples of such extenders may include diacids, diamines, or any other compound including two or more identical or different oxirane-reactive groups (e.g., hydroxyl groups, acid groups, or amine groups). Examples of extenders having two or more different oxirane-reactive groups include para hydroxyl benzoic acid and/or para hydroxy phenyl acetic acid. In some embodiments, catechol, hydroquinone, resorcinol, a substituted variant thereof, or mixtures thereof, are preferred extenders for use with polyepoxides of the present disclosure.

In other embodiments, a polyphenol of the present disclosure (e.g., a diphenol of Formula (III)) is reacted with an epihalohydrin (e.g., epichlorohydrin) to build molecular weight and produce a polyether polymer. An example of such a process is the so-called "taffy" process, which is described in detail in U.S. Pat. No. 10,113,027.

In other embodiments, a polyphenol of the present disclosure (e.g., a diphenol of Formula (II)) is reacted with one or more diepoxides other than a diepoxide of Formula (IV). Examples of such diepoxides may include diepoxides (preferably diglycidyl ethers) of aliphatic or cycloaliphatic diols, with cycloaliphatic diols being preferred in some embodiments. Examples of suitable cycloaliphatic diols may include diols having one, two, three, or more cyclic groups such as cyclohexane dimethanol, tricyclodecane dimethanol, 2,2,4,4,-tetramethyl-1,3-cyclobutanediol, isosorbide, substituted variants thereof, and mixtures thereof. Additionally, or alternatively, any of the diepoxides described in the following may be used: U.S. Pat. No. 9,409,219 (e.g., the diglycidyl ether of an ortho substituted diphenol such as 4,4-methylenebis(2,6-dimethylphenol)), WO2013/119686 (e.g., the diglycidyl ether of a dihydric monophenol such as a substituted hydroquinone), WO2015/057932 (e.g., a diepoxide of a diphenol including two or more amide linkages), WO2015/179064 (e.g., diepoxides, such as diglycidyl ethers, of: furan, benzene dimethanol, vanillyl alcohol, and diols with pendant aryl groups), WO2017/079437, WO2018/125895 (e.g., the diepoxide of a polyphenol that is the reaction product of a monophenol with a polyolefinic terpene), and U.S. Prov. Appl. No. 62/941,013.

Preferred binder polymers of the present disclosure for use in food or beverage can coating applications may be linear or branched polymers. Preferred polyester and polyether polymers, prior to any optional grafting on of water-dispersing portions (e.g., acid-functional acrylic portions) are typically linear or substantially linear polymers. Examples of processes and acid-functional acrylics for rendering polyesters or polyethers water-dispersible are described, for example, in U.S. Pat. Nos. 4,212,781, 4,285,847, 4,517,322, 5,830,952, 8,927,075, 10,501,639, U.S. Pub. No. 2005/0196629, and WO2019046750. The resulting copolymers typically have an acid number of at least 40, at least 55, or at least 70 milligrams KOH per gram of the polymer. Acid numbers referred to herein may be calculated pursuant to BS EN ISO 3682-1998 standard, or alternatively may be theoretically determined based on the reactant monomers.

If desired, one or more additional comonomers or co-oligomers may also be included with the reactants used to generate the disclosed polymers such as, e.g., diacid monomers. The comonomers or co-oligomers may, for example, be included in an initial reaction mixture of polyphenol compound and extender(s) or may be post-reacted with the resulting oligomer or polymer. In presently preferred embodiments, such additional comonomers or co-oligomers are not utilized to produce the disclosed polymers.

Molecular weight advancement of the polymer may be enhanced by the use of a suitable catalyst in an amount sufficient to facilitate the desired reaction. Examples of suitable catalysts may include phosphines, aliphatic or cycloaliphatic amines, and combinations thereof.

In preferred embodiments, the disclosed polymer includes a plurality of segments derived from the polyphenol compound described herein (e.g., the polyphenol compound of Formulas (III) or (IV)), which are preferably dispersed throughout the backbone of the polymer, more preferably a polyether backbone. In preferred embodiments, the segments derived from the polyphenol compound (termed "polyphenol segments") constitute a substantial portion of the overall mass of the polymer. Typically, the polyphenol segments constitute at least 10 wt-%, preferably at least 30 wt-%, more preferably at least 40 wt-%, even more preferably at least 50 wt-% or at least 55 wt-% of the polymer.

In some embodiments, the weight percent of the polyphenol segments in the polymer may be below the amounts recited above, and can even be substantially below. By way of example, the concentration of polyphenol segments may be outside the ranges recited above if the polymer includes large molecular weight additional components such as may occur, for example, when the polymer is a copolymer such as an acrylic-containing copolymer (e.g., an acrylic-polyether copolymer formed by grafting acrylic onto a polyether polymer of the present disclosure to, for example, render the polyether polymer water-dispersible).

The disclosed upgraded molecular weight polymers may be applied to a variety of substrates as liquid or powder-based coating compositions. Liquid coating compositions (typically including the polymer and a liquid carrier) may be preferred for many end uses, especially for use on heat-sensitive substrates or for substrates where an especially thin coating is desired. Exemplary liquid carriers include water, organic solvents, and mixtures of liquid carriers. Exemplary organic solvents include glycol ethers, alcohols, aromatic or aliphatic hydrocarbons, dibasic esters, ketones, esters, and the like. Preferably, such carriers are selected to provide a dispersion or solution of the polymer with which additional additives may be combined to provide a final coating formulation.

In one embodiment, the disclosed liquid coating compositions are solvent-based systems that include no more than a de minimis amount of water (e.g., less than 2 wt-% of water). The disclosed solvent-based liquid coating compositions may, for example, contain 10 wt-% or more, 15 wt-% or more, 20 wt-% or more of non-volatile components (viz., "solids"), and more preferably at least 25 wt-% non-volatile components. The disclosed solvent-based liquid coating compositions may also, for example, contain no greater than 50 wt-% non-volatile components or no greater than 40 wt-% non-volatile components.

In one embodiment, the coating composition is a water-based composition preferably having 10 wt-% or more or 15 wt-% or more of non-volatile components. In one embodiment, the coating composition is a water-based composition preferably having no greater than 50 wt-% non-volatile components, and more preferably no greater than 40 wt-% non-volatile components. Water-based coating systems of the present disclosure may optionally include one or more organic solvents, which will typically be selected to be miscible in water. The liquid carrier system of water-based coating compositions will typically include at least 50 wt-% of water, more typically at least 75 wt-% of water, and in some embodiments more than 90 wt-% or 95 wt-% of water. Any suitable means may be used to render the disclosed polymers miscible in water. For example, the polymers may include a suitable amount of salt groups such as anionic or cationic salt groups to render the polymers miscible in water (or groups capable of forming such salt groups). Neutralized acid or base groups are preferred salt groups. In some such embodiments, the polymer is a water-dispersible polymer having an acid number of at least 40, at least 55, or at least 70 milligrams KOH per gram of the polymer.

The disclosed polymers may serve as a binder polymer in the disclosed coating compositions. The coating composition may be, for example, suitable for use as a coating for container, such as a food or beverage container. The binder polymer amount may vary widely depending on a variety of considerations including the method of application, the presence of other film-forming materials, whether the coating composition is a water-based or solvent-based system, and so on. For liquid-based coating compositions, the binder polymer will typically constitute at least 10 wt-%, more typically at least 30 wt-%, and even more typically at least 50 wt-% of the coating composition, based on the total weight of resin solids in the coating composition. For such liquid-based coating compositions, the binder polymer will typically constitute less than about 90 wt-%, more typically less than about 80 wt-%, and even more typically less than about 70 wt-% of the coating composition, based on the total weight of resin solids in the coating composition.

The disclosed coating compositions may be present as a layer of a mono-layer coating system or as one or more layers of a multi-layer coating system. The coating composition can be used as a primer coat, an intermediate coat, a top coat, or a combination thereof. The coating composition may be, for example, suitable for use as a coating for container, such as a food or beverage container. The coating thickness of a particular layer and of the overall coating system will vary depending upon the coating material used, the substrate, the coating application method, and the end use for the coated article. Mono-layer or multi-layer coating systems including one or more layers formed from the disclosed coating composition may have any suitable overall coating thickness, but in packaging coating applications (e.g., food or beverage containers or portions thereof) will typically have an overall average dry coating thickness of from about 2 to about 60 micrometers and more typically from about 3 to about 12 micrometers.

Figure 8:
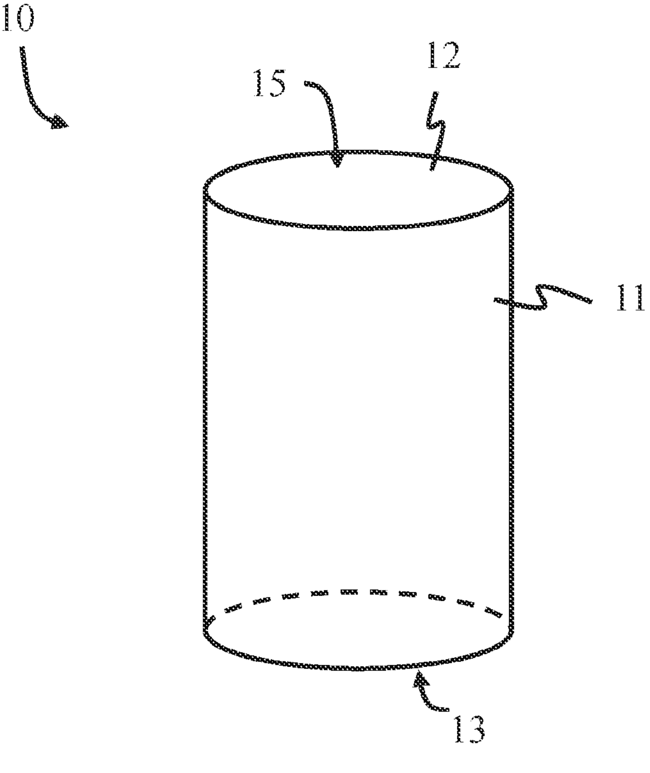
FIG. 8 is a is a schematic illustration of a food or beverage container having a coating formed from the coating composition of the present disclosure.

For instance, FIG. 8 shows a container 10, which is a simplified example of a food or beverage container that may be coated with the coating composition of the present disclosure. The container 10 may be a two-piece can or a three-piece can. The container 10 has side wall 11, a first end 12 (e.g., a top), and a second end 13 (e.g., a bottom), defining an interior 15. In a two-piece can, the side wall 11 and one of the ends (e.g., the second end 13) may be formed of a continuous piece. The container 10 may be made of a metal substrate. The metal substrate may be coated with the coating composition of the present disclosure.

The disclosed coating compositions may be applied to a substrate (typically a metal substrate) either prior to, or after, the substrate is formed into an article such as, for example, a food or beverage container or a portion thereof. In one embodiment, a method of forming food or beverage cans is provided that includes: applying a coating composition described herein to a metal substrate (e.g., applying the composition to the metal substrate in the form of a planar coil or sheet), hardening the composition, and forming (e.g., via stamping) the substrate into a packaging container or a portion thereof (e.g., a food or beverage can or a portion thereof). For example, two-piece or three-piece cans or portions thereof such as riveted beverage can ends with a cured coating of the disclosed coating composition on a surface thereof can be formed in such a method. In another embodiment, a method of forming food or beverage cans is provided that includes: forming (e.g., via stamping) a metal substrate into a packaging container or a portion thereof (e.g., a food or beverage can or a portion thereof), applying a coating composition described herein to the inside, outside or both inside and outside portions of such packaging container or a portion thereof, and hardening the composition. For example, the coating composition may be spray applied to an interior surface of a preformed food or beverage can (e.g., as typically occurs with "two-piece" food or beverage cans). The disclosed upgraded molecular weight polymers are especially desirable for use on the inside or interior portion of such food or beverage containers, and for other applications involving a food or beverage contact surface or involving a metal substrate. Exemplary such applications include two-piece drawn food cans, three-piece food cans, food can ends, drawn and ironed food or beverage cans, beverage can ends, easy open can ends, twist-off closure lids, and the like.

Suitable metal substrates include, for example, steel or aluminum. The metal substrate used in forming rigid food or beverage cans, or portions thereof, typically has a thickness in the range of about 0.005 inches to about 0.025 inches. Electro tinplated steel, cold-rolled steel, and aluminum are commonly used as metal substrates for food or beverage cans, or portions thereof. In embodiments in which a metal foil substrate is employed in forming, e.g., a packaging article, the thickness of the metal foil substrate may be even thinner that that described above.

The coating composition can be applied to a substrate using any suitable procedure such as spray coating, roll coating, coil coating, curtain coating, immersion coating, meniscus coating, kiss coating, blade coating, knife coating, dip coating, slot coating, slide coating, and the like, as well as other types of premetered coating. Where the coating is used to coat metal sheets or coils, the coating can be applied by roll coating.

After applying the coating composition onto a substrate, the composition can be cured using a variety of processes, including, for example, oven baking by either conventional or convection methods, or any other method that provides an elevated temperature suitable for curing the coating. The curing process may be performed in either discrete or combined steps. For example, substrates can be dried at ambient temperature to leave the coating compositions in a largely uncrosslinked state. The coated substrates can then be heated to fully cure the compositions. In certain instances, the disclosed coating compositions may be dried and cured in one step. The cure conditions will vary depending upon the method of application and the intended end use. The curing process may be performed at any suitable temperature, including, for example, oven temperatures in the range of from about 100° C. to about 300° C., and more typically from about 177° C. to about 250° C. If a metal coil is the substrate to be coated, curing of the applied coating composition may be conducted, for example, by heating the coated metal substrate over a suitable time period to a peak metal temperature ("PMT") of preferably greater than about 177° C. More preferably, the coated metal coil is heated for a suitable time period (e.g., about 5 to 900 seconds) to a PMT of at least about 218° C.

According to an embodiment, the polymer is a copolymer including a phenol pendant obtained by reacting an aromatic compound comprising an aromatic ring and a hydroxyl directly linked to the aromatic ring, and a carbonyl group; with a polymer containing a functional unit comprising a carbonyl group. The preferred polymer is acrylic containing methacrolein, HMF methacrylate, and/or vanillin methacrylate units.

In some embodiments, the monomer is further reacted to introduce one or more vinylic double bonds. For example, the example the diepoxide monomer can be reacted with a (meth)acrylic acid monomer to introduce a vinylic double bond for subsequent free-radical reaction to form, for example, an acrylic polymer. Such acrylics may be organic solution polymerized acrylics or emulsion polymerized latex acrylics.

In some embodiments, the polymer (particularly a polyether) made with one or more of the monomers of the present disclosure has a backbone that includes (i) terminal oxirane end groups, (ii) terminal phenolic groups, or (iii) both (i) and (ii).

In preferred embodiments, the polymer (e.g., a polyether polymer) made with one or more of the monomers of the present disclosure includes a plurality of secondary hydroxyl groups attached to a backbone of the polymer. Examples of preferred secondary hydroxyl groups includes those present in $-CH_2-CH(OH)-CH_2-$ or $-CH_2-CH_2-CH(OH)-$ backbone segments. Thus, in particularly preferred embodiments, the polymer includes one or more such backbone segments and more preferably a plurality of such backbone segments.

In preferred embodiments, the polymer (e.g., a polyether polymer) made with one or more of the monomers of the present disclosure, which may form part of a coating composition, has a number average molecular weight of 2000 or greater, 3000 or greater, 3500 or greater, or 4000 or greater. The number average molecular weight of the polymer may have any suitable upper limit, such as up to 100,000, up to 50,000, up to 20,000, or up to 10,000.

In preferred embodiments, the polymer (e.g., a polyether polymer) made with one or more of the monomers of the present disclosure has a polydispersity index ("PDI") of 1.5 or greater or 2 or greater. The PDI of the polymer may be 5 or less, or 3.5 or less. In some cases, the PDI is from about 1.5 to about 5, more preferably from about 2 to about 3.5.

The disclosed polymers can have any suitable glass transition temperature ("Tg"). As discussed above, in certain preferred embodiments, the coating composition disclosed herein is suitable for use in forming a food-contact packaging coating such as, for example, an interior food or beverage can coating. To exhibit a suitable balance of coating properties for use as a food-contact packaging coating, including suitable corrosion resistance when in prolonged contact with packaged food or beverage products which may be of a corrosive nature, the disclosed polymers preferably have a Tg of more than 0° C., more preferably at least 30° C., at least 40° C., at least 50° C., at least 60° C., or at least 70° C. In such preferred embodiments, the Tg is less than 150° C., more preferably less than 130° C., and even more preferably less than 110° C. Tg can be measured via differential scanning calorimetry ("DSC"). In particularly preferred embodiments, the polymer is a polyether polymer exhibiting a Tg pursuant to the aforementioned Tg values.

When the Tg of a polymer is referenced herein in the context of a coating composition including the polymer or a coated article coated with such a coating composition, the indicated Tg values for the polymer refers to the Tg of the polymer prior to any cure of a coating composition including the polymer.

While not intending to be bound by any theory, when a "high" Tg polymer is desired, the desired Tg may be achieved, for example, by selecting a suitable amount of one or more monomers that tend to yield a higher Tg polymer. Examples of such monomers may include certain monomers having one or more aryl or heteroaryl groups, one or more polycyclic groups, and/or one or more alicyclic groups such as, e.g., cyclobutane groups, tricyclodecane groups, and the like.

In some embodiments, the monomer (e.g., diphenol and/or diepoxide monomer) is used to prepare a coating composition. The coating composition may include 5 wt-% or more, 10 wt-% or more, 20 wt-% or more, 35 wt-% or more, 50 wt-% or more, 65 wt-% or more, 80 wt-% or more, 90 wt-% or more, or 95 wt-% or more, or even 99 wt-% or more of polymer made from monomers of the present disclosure, based on total resin solids included in the coating composition. In some embodiments, the coating composition includes 100 wt-% or less, 95 wt-% or less, 90 wt-% or less, 80 wt-% or less, 60 wt-% or less, 40 wt-% or less, 20 wt-% or less, 10 wt-% or less of polymers made from monomers of the present disclosure, based on total resin solids included in the coating composition. The coating composition may be, for example, suitable for use as a coating for container, such as a food or beverage container.

In preferred embodiments, the monomer (e.g., diphenol and/or diepoxide monomer) constitutes 1 wt-% or more, 2 wt-% or more, 5 wt-% or more, 10 wt-% or more, 20 wt-% or more, 35 wt-% or more, 50 wt-% or more, 65 wt-% or more, 80 wt-% or more, 90 wt-% or more, or 95 wt-% or more, or 99 wt-% or more of the monomers used to make the polymer. The diphenol or diepoxide monomer may constitute 100 wt-% or less, 95 wt-% or less, 90 wt-% or less, 80 wt-% or less, 60 wt-% or less, 50 wt-% or less, 40 wt-% or less, 20 wt-% or less, or 10 wt-% or less of the monomers used to make the polymer. In some embodiments, the diphenol or diepoxide monomer constitutes 25 wt-% to 100 wt-%, or 40 wt-% to 100 wt-% of the polymer.

In some embodiments the diphenol or diepoxide monomer or a polymer made with the monomer may be included in a coating composition in an amount consistent with being used as a formulation additive (e.g., as an adhesion promoter). In other embodiments, the diphenol or diepoxide monomer or a polymer made with the monomer may be included in a substantial or predominant amount of a coating composition, such as a film-forming resin system of the coating composition.

When the disclosed coating compositions include polymers having suitable reactive groups (for example, amino groups, phenyl hydroxyl groups, carboxylic acid or anhydride groups, and/or ethylenically unsaturated groups), the coating composition may also be formulated using one or more optional (e.g., additional) curing agents (for example, crosslinking resins, sometimes referred to as "crosslinkers"). The choice of a particular crosslinking agent (sometimes referred to as a "crosslinking resin" or "crosslinker"), if used, typically will depend on the particular product being formulated. For example, some coatings are highly colored (e.g., gold-colored coatings). These coatings may typically be formulated using crosslinkers that themselves tend to have a yellowish color. Preferred crosslinking agents are substantially free of BPA, BPF, BPS, glycidyl ether compounds thereof (e.g., BADGE), and epoxy novolacs. Any of a variety of hydroxyl-reactive, oxirane-reactive, or carboxyl-reactive crosslinking agents may be used, including phenoplast, aminoplast and blocked or non-blocked isocyanate crosslinking agents, polyamines, beta-hydroxy alkylamides (e.g., the PRIMID XL-552 and QM-1260 products by EMS-CHEMIE AG), as well as combinations thereof. Exemplary phenoplast resins include the condensation products of aldehydes with phenols, with formaldehyde and acetaldehyde being preferred aldehydes. Exemplary phenols include phenol, cresol, p-phenylphenol, p-tert-butylphenol, p-tert-amylphenol, and cyclopentylphenol. Exemplary aminoplast resins include the condensation products of aldehydes such as formaldehyde, acetaldehyde, crotonaldehyde, and benzaldehyde with amino or amido group containing substances such as urea, melamine, and benzoguanamine. Examples of suitable aminoplast crosslinking resins include benzoguanamine-formaldehyde resins, melamineformaldehyde resins, esterified melamineformaldehyde, and urea-formaldehyde resins. One specific example of a suitable aminoplast crosslinker is the fully alkylated melamineformaldehyde resin commercially available from Cytec Industries, Inc. under the trade name of CYMEL 303. Exemplary blocked or non-blocked isocyanates include aliphatic, cycloaliphatic or aromatic di-, tri-, or poly-valent isocyanates, such as hexamethylene diisocyanate (HMDI), cyclohexyl-1,4-diisocyanate, and the like. Further examples of generally suitable blocked isocyanates include isomers of isophorone diisocyanate, dicyclohexylmethane diisocyanate, toluene diisocyanate, diphenylmethane diisocyanate, phenylene diisocyanate, tetramethyl xylene diisocyanate, xylylene diisocyanate, and mixtures thereof. In some embodiments, blocked isocyanates are used that have a number-average molecular weight of at least about 300, more preferably at least about 650, and even more preferably at least about 1,000.

The concentration of crosslinking agent in the coating composition may depend on the type of crosslinking agent, the time and temperature of the bake, and the molecular weights of the copolymer particles. When used, the crosslinker is typically present in an amount of up to about 50% by weight, preferably up to about 30% by weight, and more preferably up to about 15% by weight. When used, the crosslinker is typically present in an amount of at least about 0.1% by weight, more preferably at least about 1% by weight, and even more preferably at least about 1.5% by weight. These weight percentages are based on the total resin solids weight of the coating composition.

In some embodiments, the coating composition is substantially free of formaldehyde and formaldehyde-containing materials, more preferably essentially free of these compounds, even more preferably essentially completely free of these compounds, and most preferably completely free of these compounds.

The disclosed coating compositions may also include other optional ingredients or additives that do not adversely affect the coating composition or cured coating thereof. Such optional ingredients are typically included in a coating composition to enhance composition esthetics; to facilitate manufacturing, processing, handling, or application of the composition; or to further improve a particular functional property of a coating composition or a cured coating thereof. For example, the disclosed coating compositions may optionally include fillers other than those already mentioned, dyes, colorants, toners, coalescents, extenders, anticorrosion agents, flow control agents, thixotropic agents, dispersing agents, antioxidants, oxygen-scavenging materials, adhesion promoters, light stabilizers, and mixtures thereof, selected to provide desired film properties. Each optional ingredient is preferably included in a sufficient amount to serve its intended purpose, but not in such an amount to adversely affect a coating composition or a cured coating thereof.

The disclosed coating compositions may also include other optional polymers that do not adversely affect the coating composition or a cured coating thereof. Such optional polymers are typically included as a nonreactive filler material, although they may be included as a reactive crosslinker, or to provide other desired properties. Such optional nonreactive filler polymers include, for example, polyesters, acrylics, polyamides, and polyethers. Alternatively, such additional polymeric materials or monomers may be reactive with other components of the composition (e.g., an acid-functional or unsaturated polymer). If desired, reactive polymers may be incorporated into the disclosed compositions, for example to provide additional functionality for various purposes, including crosslinking or to assist in dispersing the disclosed upgraded molecular weight polymers into water. Examples of such reactive polymers include, for example, functionalized polyesters, acrylics, polyamides, and polyethers.

Another preferred optional ingredient is a catalyst to increase the rate of cure. Examples of catalysts, include, but are not limited to, strong acids including phosphoric acid, dodecylbenzene sulfonic acid (DDBSA, available as CYCAT 600 from Cytec), methane sulfonic acid (MSA), p-toluene sulfonic acid (pTSA), dinonylnaphthalene disulfonic acid (DNNDSA), and triflic acid; quaternary ammonium compounds; phosphorous compounds; and tin, titanium, and zinc compounds; sources of free radicals (e.g., peroxides, azoic compounds, and the like). Specific examples include, but are not limited to, a tetraalkyl ammonium halide, a tetraalkyl or tetraaryl phosphonium iodide or acetate, tin octoate, zinc octoate, triphenylphosphine, and similar catalysts known to persons having ordinary skill in the art. If used, a catalyst is preferably present in an amount of at least 0.01 wt-%, and more preferably at least 0.1 wt-%, based on the weight of nonvolatile material in the coating composition. If used, a catalyst is preferably present in an amount of no greater than 3 wt-%, and more preferably no greater than 1 wt-%, based on the weight of nonvolatile material in the coating composition.

If used, the catalyst is preferably present in an amount of at least about 0.01% by weight, and more preferably at least about 0.1% by weight, based on the total solids weight of the coating composition. Furthermore, if used, the catalyst is also preferably present in a nonvolatile amount of no greater than about 3% by weight, and more preferably no greater than about 1% by weight, based on the total solids weight of the coating composition.

Another useful optional ingredient is a lubricant (e.g., a wax), which facilitates manufacture of fabricated metal articles (e.g., container closures and food or beverage can ends) by imparting lubricity to sheets of coated metal substrate. Non-limiting examples of suitable lubricants include, for example, natural waxes such as Carnauba wax or lanolin wax, polytetrafluoroethane (PTFE) and polyethylene-type lubricants. If used, a lubricant is preferably present in the coating composition in an amount of at least 0.1 wt-%, and preferably no greater than 2 wt-%, and more preferably no greater than 1 wt-%, based on the total weight of nonvolatile material in the coating composition.

Surfactants may optionally be added to the disclosed coating composition to aid in flow and wetting of a substrate. Examples of surfactants include, but are not limited to, nonylphenol polyethers and salts and similar surfactants known to persons having ordinary skill in the art. If used, a surfactant is preferably present in an amount of at least 0.01 wt-%, and more preferably at least 0.1 wt-%, based on the weight of resin solids. If used, a surfactant is preferably present in an amount no greater than 10 wt-%, and more preferably no greater than 5 wt-%, based on the weight of resin solids.

Another useful optional ingredient is a pigment, such as titanium dioxide. If used, a pigment is present in the coating composition in an amount of no greater than about 70% by weight, more preferably no greater than about 50% by weight, and even more preferably no greater than about 40% by weight, based on the total solids weight of the coating composition.

In preferred embodiments, the coating composition is substantially free or completely free of any structural units derived from bisphenol A ("BPA"), bisphenol F ("BPF"), bisphenol S ("BPS"), or any diepoxides thereof (e.g., diglycidyl ethers thereof such as the diglycidyl ether of BPA ("BADGE")). In addition, the coating composition is preferably substantially free or completely free of any structural units derived from a dihydric phenol, or other polyhydric phenol, having estrogenic agonist activity great than or equal to that of 4,4'-(propane-2,2-diyl)diphenol. More preferably, the coating composition is substantially free or completely free of any structural units derived from a dihydric phenol, or other polyhydric phenol, having estrogenic agonist activity greater than or equal to that of BPS. In some embodiments, the coating composition is substantially free or completely free of any structural units derived from a bisphenol.

Even more preferably, the coating composition is substantially free or completely free of any structural units derived from a dihydric phenol, or other polyhydric phenol, having estrogenic agonist activity greater than 4,4'-(propane-2,2-diyl)bis(2,6-dibromophenol). Optimally, the coating composition is substantially free or completely free of any structural units derived from a dihydric phenol, or other polyhydric phenol, having estrogenic agonist activity greater than 2,2-bis(4-hydroxyphenyl)propanoic acid. The same is preferably true for any other components of a composition including the coating composition. See, for example, U.S. Pat. No. 9,409,219 for a discussion of such structural units and applicable test methods.

In some further embodiments, the coating composition is substantially free or completely free of any acrylamide-type monomers (e.g., acrylamides or methacrylamide). Moreover, in some embodiments, the coating composition is substantially free or completely free of one or more of styrene (whether free or polymerized) or substituted styrene compounds (whether free or polymerized). As discussed above, in these embodiments, the reactant monomers may include other ethylenically-unsaturated aromatic compounds or ethylenically unsaturated alicyclic compounds, such as aromatic (meth)acrylates or alicyclic (meth)acrylates, for example. In additional further embodiments, the coating composition is substantially free or completely free of halogenated monomers (whether free or polymerized), such as chlorinated vinyl monomers.

The coating composition may also optionally be rheologically modified for different coating applications. For example, the coating composition may be diluted with additional amounts of the aqueous carrier to reduce the total solids content in the coating composition. Alternatively, portions of the aqueous carrier may be removed (e.g., evaporated) to increase the total solids content in the coating composition. The final total solids content in the coating composition may vary depending on the particular coating application used (e.g., spray coating), the particular coating use (e.g., for interior can surfaces), the coating thickness, and the like.

In some embodiments, the coating composition preferably has a total solids weight greater than about 5%, more preferably greater than about 10%, and even more preferably greater than about 15%, based on the total weight of the coating composition. In liquid embodiments, the coating composition also preferably has a total solids weight less than about 80%, more preferably less than about 60%, and even more preferably less than about 50%, based on the total weight of the coating composition. The liquid carrier (e.g., aqueous or organic solvent carrier) may constitute the remainder of the weight of the coating composition. In certain spray coating applications (e.g., inside spray for food or beverage cans including, e.g., aluminum beverage cans), the coating composition may have a total solids weight of less than about 40%, more preferably less than about 30%, and even more preferably less than about 25%, based on the total weight of the coating composition. In some of these embodiments, the coating composition may have a total solids weight ranging from about 18% to about 22%. The aqueous carrier may constitute the remainder of the weight of the coating composition.

As previously discussed, the aqueous carrier of the coating composition preferably includes water and may further include one or more optional organic solvents. In some embodiments, water constitutes greater than about 20% by weight, more preferably greater than about 35% by weight, and even more preferably greater than about 50% by weight of the total weight of the aqueous carrier. In some embodiments, water constitutes 100% or less, more preferably less than about 95% by weight, and even more preferably less than about 90% by weight of the total weight of the aqueous carrier.

While not intending to be bound by theory, the inclusion of a suitable amount of an organic solvent can be advantageous in some embodiments (e.g., for certain coil coating applications to modify flow and leveling of the coating composition, control blistering, and maximize the line speed of the coil coater). Accordingly, in certain embodiments, the organic solvents may constitute greater than 0%, more preferably greater than about 5%, and even more preferably greater than about 10% by weight of the aqueous carrier, based on the total weight of the aqueous carrier. In these embodiments, the organic solvents may also constitute less than about 80%, more preferably less than about 50%, and even more preferably less than about 40% by weight of the aqueous carrier, based on the total weight of the aqueous carrier.

The coating composition preferably has a viscosity suitable for a given coating application. In some embodiments, such as for certain spray coating applications, the coating composition may have an average viscosity greater than about 5 seconds, more preferably greater than 10 seconds, and even more preferably greater than about 15 seconds, based on the Viscosity Test described below (Ford Viscosity Cup #4 at 25° C.). In some embodiments, the coating composition may also have an average viscosity less than about 40 seconds, more preferably less than 30 seconds, and even more preferably less than about 25, based on the Viscosity Test described below.

The coating composition of the present disclosure with the aqueous dispersion of the copolymer particles may be applied on a variety of different substrates using a variety of different coating techniques. In some embodiments, the coating composition is applied by roll coating, e.g., in the case of sheet fed and coil applications. In some embodiments, the coating composition is applied as an inside spray coating. As briefly described above, cured coatings formed from the coating composition are particularly suitable for use on metal food and beverage cans (e.g., two-piece cans, three-piece cans, and the like). Two-piece cans (e.g., two-piece beer or soda cans and certain food cans) are typically manufactured by a drawn and ironing ("D&I") process. The cured coatings are also suitable for use in food or beverage contact situations (collectively referred to herein as "food-contact") and may be used on the inside or outside of such cans.

Preferred inside spray or roller coat coating compositions of the present disclosure are capable of being spray applied on an interior of a food or beverage can (e.g., a 3-piece or 2-piece food or beverage can) to effectively, and evenly, coat the substrate and form a continuous cured coating (e.g., the substrate has been effectively coated and is free of unsuitable holes or other discontinuities in the coating).

Suitable curing temperatures for the coating composition of the present disclosure, in particular coating compositions used for can coating, are greater than about 150° C. (about 300° F.), more preferably greater than about 165° C. (about 330° F.), and even more preferably greater than about 180° C. (about 360° F.). In some embodiments, suitable curing temperatures for the coating composition of the present disclosure are also less than about 250° C. (about 480° F.), more preferably less than about 240° C. (about 460° F.), and even more preferably less than about 230° C. (about 450° F.). Suitable oven residence times for the above-discussed temperatures range from about 10 seconds to about 30 minutes. For example, in some applications, such as coil coatings, the oven residence time may be less than 1 minute, such as 10 seconds to 30 seconds. In some applications, such as inside spray applications, the oven residence time may be more than 1 minute, such as from 1 minute to 2 minutes. In some applications, such as interior food can coatings, the oven residence time may be more than 5 minutes, such as from 10 to 30 minutes. After curing, the resulting cured can coatings may have suitable film thicknesses for protecting the cans from food or beverage products that are subsequently filled into the cans.

The desired film thickness for the cured coating may vary depending on the particular food or beverage to be filled in a given can. In some embodiments for the spray coating application (e.g., inside spray for food or beverage cans), the average film thickness after curing is greater than about 0.7 milligrams/square-inch (mg/inch$^2$), more preferably greater than about 0.8 mg/inch$^2$, and even more preferably greater than about 0.9 mg/inch$^2$. In these embodiments, the average film thickness after curing is also less than about 4.0 mg/inch$^2$, more preferably less than about 3.0 mg/inch$^2$, and even more preferably less than about 2.5 mg/inch$^2$. For a sheet fed application, the maximum average film thickness is preferably about 5.5 mg/inch$^2$ or less, or about 5.2 mg/inch$^2$ or less.

In some further embodiments, the average film thickness after curing ranges from about 0.9 mg/inch$^2$ to about 1.1 mg/inch$^2$. In other further embodiments, the average film thickness after curing ranges from about 1.4 mg/inch$^2$ to about 1.6 mg/inch$^2$. In yet other further embodiments, the average film thickness after curing ranges from about 1.9 mg/inch$^2$ to about 2.1 mg/inch$^2$.

Alternatively, the coating composition may optionally be applied as a coil coating. During a coil coating application, a continuous coil composed of a metal (e.g., steel or aluminum) is coated with the coating composition of the present disclosure. Once coated, the coating coil may be subjected to a short thermal, ultraviolet, or electromagnetic curing cycle, for hardening (e.g., drying and curing) of the coating composition. Coil coatings provide coated metal (e.g., steel or aluminum) substrates that can be fabricated into formed articles, such as two-piece drawn food cans, food can ends, beverage can ends, and the like.

The coating composition of the present disclosure also offers utility in other coating applications. These additional applications include, but are not limited to, wash coating, sheet coating, and side seam coatings (e.g., food can side seam coatings). Other commercial coating application and curing methods are also envisioned, for example, electrocoating, extrusion coating, laminating, powder coating, and the like. The coating composition may also be useful in medical or cosmetic packaging applications, including, for example, on surfaces of metered dose inhalers ("MDIs"), including on drug-contact surfaces.

During the above-discussed curing steps, the solvent system is preferably vaporized or otherwise dried off from the coating, allowing the polymer or copolymer molecules to cure. If desired, the drying and curing steps may be combined in a single step or carried out in separate steps.

Preferred glass transition temperatures for the cured coating of the present disclosure (and particularly interior, food-contact coatings) include those greater than about 50° C., more preferably greater than about 60° C., even more preferably greater than about 70° C., and in some embodiments, greater than about 80° C. Preferred glass transition temperatures for the cured coating include those less than about 120° C., more preferably less than about 115° C., even more preferably less than about 110° C., and in some embodiments, less than about 100° C. The glass transition temperatures can be measured by differential scanning calorimetry (DSC).

To further prevent or otherwise reduce coating penetration by an intended food or beverage product, the cured coating is preferably suitably hydrophobic. For example, the cured coating can have a contact angle with deionized water greater than about 90, more preferably greater than about 95, and even more preferably greater than about 100.

The cured coating may exhibit desired properties for use as an inside spray coating for food and beverage containers. For example, the cured coating preferably gives a global extraction of less than about 25 parts-per-million (ppm), and more preferably less than about 10 ppm, and even more preferably less than about 1 ppm, pursuant to the Global Extraction test below.

Moreover, the coating composition (uncured) should preferably exhibit substantially no change (e.g., a change in viscosity, if any, of less than 25%, more preferably less than 10%, even more preferably less than 5%, and even more preferably less than 1%) in viscosity pursuant to the Pot Life Stability test below. Accordingly, the coating composition of the present disclosure is particularly suitable for use as a sheet fed coating or an inside spray coating composition for containers configured to retain a variety of different food or beverage products.

The purity of the composition and the identity of the monomer may be determined using any suitable analytical technique. For example, proton NMR may be used to identify the monomer. An example of a useful quantitative technique is gas chromatography (GC) combined with a suitable detection method, such as mass spectrometry (MS). GC-MS may be complemented with liquid chromatography (LC) and an ultraviolet-visible light detector (UV-Vis) if impurities or other components are difficult to detect using GC-MS.

Test Methods

The disclosed coating compositions may be evaluated using a variety of test methods, including the following.

Solvent Resistance Test. The extent of "cure" or crosslinking of a coating is measured as a resistance to solvents, such as methyl ethyl ketone (MEK). This test is performed as described in ASTM D 5402-93. The number of double rubs (viz., one back-and-forth motion) is reported. Preferably, the MEK solvent resistance is at least 30 double rubs.

Retort Method. This test provides an indication of an ability of a coating to withstand conditions frequently associated with food or beverage preservation or sterilization. Coated ETP flat panels may be placed in a vessel and partially immersed in a test substance. While totally immersed in the test substance, the coated substrate samples are placed in an autoclave and subjected to heat of 130° C. and pressure of 1 atmosphere above atmospheric pressure for a time period of 60 minutes. Just after retort, the coated substrate samples are tested for metal exposure.

Wedge Bend Test. This test provides an indication of a level of flexibility of a coating and its extent of cure. Test wedges are formed from coated 12 cm long by 5 cm wide rectangular metal test sheets. Test wedges are formed from the coated sheets by folding (viz., bending) the sheets around a mandrel. To accomplish this, the mandrel is positioned on the coated sheets so that it is oriented parallel to, and equidistant from, the 12 cm edges of the sheets. The resulting test wedges have a 6 mm wedge diameter and a length of 12 cm. To assess the wedge bend properties of the coatings, the test wedges are positioned lengthwise in a metal block of a wedge bend tester and a 2.4 kg weight is dropped onto the test wedges from a height of 60 cm. The deformed test wedges are then immersed in a copper sulphate test solution (prepared by combining 20 parts of $CuSO_4 \cdot 5H_2O$, 70 parts of deionized water, and 10 parts of hydrochloric acid (36%)) for about 2 minutes. The exposed metal is examined under a microscope and the millimeters of coating failure along the deformation axis of the test wedges is measured. The results may be expressed as a wedge bend percentage using the following calculation:

$$100\% \times [(120\ \text{mm}) - (\text{mm of failure})]/(120\ \text{mm}).$$

A coating is considered to satisfy the Wedge Bend Test if it exhibits a wedge bend percentage of 70% or more.

Metal Exposure. This test measures the ability of a coated substrate to retain its integrity as it undergoes the formation process necessary to produce a fabricated article such as a can end. It is a measure of the presence or absence of cracks or fractures in the formed end or container. The end is typically placed on a cup filled with an electrolyte solution. The cup is inverted to expose the surface of the end to the electrolyte solution. The intensity of electrical current that passes through the end is then measured. If the coating remains intact (no cracks or fractures) after fabrication, minimal current will pass through the end. The container itself will replace the cup in the test above in case of 2 piece can.

For the present evaluation, fully converted standard food can ends were exposed for a period of approximately 4 seconds to a room-temperature electrolyte solution comprised of 1% NaCl by weight in deionized water. The coating evaluated was present on the interior surface of the end. Metal exposure was measured using a WACO Enamel Rater II (available from the Wilkens-Anderson Company, Chicago, IL) with an output voltage of 6.3 volts. The measured electrical current, in milliamps, is reported. End continuities were tested initially and then after the ends were subjected to retort. After cooling and drying, the milliamps of current passing through the end was measured again.

Preferred coatings of the present invention initially pass less than 10 milliamps (mA) when tested as described above, more preferably less than 5 mA. After retort, preferred coatings give continuities of less than 20 mA, more preferably less than 10 mA, and even more preferably less than 5 mA.

Differential Scanning calorimetry. Samples for differential scanning calorimetry ("DSC") testing are prepared by first applying the liquid resin composition onto aluminum sheet panels. The panels are then baked in a Fisher Isotemp electric oven for 20 minutes at 300° F. (149° C.) to remove volatile materials. After cooling to room temperature, the samples are scraped from the panels, weighed into standard sample pans and analyzed using the standard DSC heat-cool-heat method. The samples are equilibrated at −60° C., then heated at 20° C. per minute to 200° C., cooled to −60° C., and then heated again at 20° C. per minute to 200° C. Glass transitions are calculated from the thermogram of the last heat cycle. The glass transition is measured at the inflection point of the transition.

The invention is illustrated by the following examples. It is to be understood that the particular examples, materials, amounts, and procedures are merely illustrative and that other embodiments may be made as described. Unless otherwise indicated, all parts and percentages are by weight.

Viscosity Test. This test measures the viscosity of a coating composition for rheological purposes, such as for sprayability and other coating application properties. The test is performed pursuant to ASTM D1200-88 using a Ford Viscosity Cup #4 at 25° C. The results are measured in the units of seconds.

Global Extraction Test. The global extraction test is designed to estimate the total amount of mobile material that can potentially migrate out of a coating and into food packed in a coated can. Typically, coated substrate is subjected to water or solvent blends under a variety of conditions to simulate a given end use. Acceptable extraction conditions and media can be found in 21 CFR § 175.300 paragraphs (d) and (e). The allowable global extraction limit as defined by the FDA regulation is 50 parts per million (ppm).

The extraction procedure that can be used in the current invention is described in 21 CFR § 175.300 paragraph (e)(4)(xv) with the following modifications to ensure worst-case scenario performance: (1) the alcohol (ethanol) content is increased to 10% by weight, and (2) the filled containers are held for a 10-day equilibrium period at 37.8° C. (100° F.). These conditions are per the FDA publication "Guidelines for Industry" for preparation of Food Contact Notifications.

The coated beverage can is filled with 10% by weight aqueous ethanol and subjected to pasteurization conditions (65.6° C., 150° F.) for 2 hours, followed by a 10-day equilibrium period at 37.8° C. (100° F.). Determination of the amount of extractives is determined as described in 21 CFR § 175.300 paragraph (e) (5), and ppm values are calculated based on surface area of the can (no end) of 44 square inches with a volume of 355 milliliters. Preferred coatings should give global extraction results of less than 50 ppm, more preferred results of less than 10 ppm, even more preferred results of less than 1 ppm. Most preferably, the global extraction results are optimally non-detectable.

EXEMPLARY EMBODIMENTS

According to embodiment 1, a method of forming a monomer comprises reacting reactants comprising a first compound comprising an aromatic ring and a carbonyl group; a second compound comprising a carbonyl group; and optionally a third compound comprising an epoxide ring; wherein the monomer comprises a polyol (e.g., a polyphenol) or a polyepoxide.

Embodiment 2 is the method of embodiment 1, wherein the first compound comprises an alkoxide group directly attached to the aromatic ring.

Embodiment 3 is the method of any one of the preceding embodiments, wherein the first compound comprises a hydroxy group, which is preferably directly attached to the aromatic ring.

Embodiment 4 is the method of any one of the preceding embodiments, wherein the carbonyl group of the first compound comprises an acyl group, preferably —CH(═O) or an acetyl group, which is preferably directly attached to the aromatic ring.

Embodiment 5 is the method of any one of the preceding embodiments, wherein the first compound is of Formula (I):

Formula (I)

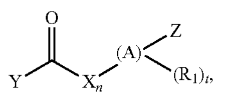

wherein A is an aromatic ring, optionally substituted and optionally including a hetero atom, wherein the hetero atom is preferably 0, N, or S; wherein each $R_1$ and Y are independently hydrogen or an organic group (e.g., an aliphatic group, a cycloaliphatic group, or an aromatic group); wherein X is an organic group (e.g., a C1-C20, C1-C10, or C1-C4-containing group such as an aliphatic group, a cycloaliphatic group, an aromatic group) or is absent (when n is 0); wherein Z is a group reactive with epichlorohydrin (e.g., a hydroxyl group or hydroxy-containing group including one or more carbon atoms); wherein n is 0 or 1; and wherein t is 2 to 4.

Embodiment 6 is the method of embodiment 3, wherein n is zero (0).

Embodiment 7 is the method of any one of the preceding embodiments, wherein Y is a hydrogen and the first compound is of Formula (IA):

Formula (IA)

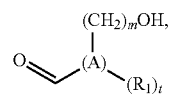

wherein A, $R_1$, and t are as in Formula (I), preferably wherein $R_1$ is hydrogen or an aliphatic group comprising oxygen; and wherein m is 0 to 2.

Embodiment 8 is the method of any one of the preceding embodiments, wherein the first compound comprises vanillin, hydroxymethyl furfural, a hydroxybenzaldehyde (e.g., 4-hydroxybenzaldehyde or 2-hydroxybenzaldehyde), a hydroxyl naphthaldehyde (e.g., 1-hydroxy-2-naphthaldehyde, 3-hydroxy-2-naphthaldehyde, or 4-hydroxy-1-naphthaldehyde), 3-hydroxyacetophenone, a substituted variant thereof, or a combination thereof, preferably wherein the first compound comprises vanillin or hydroxymethyl furfural.

Embodiment 9 is the method of any one of the preceding embodiments, wherein the second compound is of Formula (II):

Formula (II)

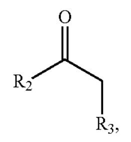

wherein $R_2$ and $R_3$ are each independently hydrogen or an organic group, (e.g., a C1-C20, C1-C10, or C1-C4-containing group such as an aliphatic group, a cycloaliphatic group, or an aromatic group), wherein optionally $R_2$ and $R_3$ are fused in a ring.

Embodiment 10 is the method of any one of the preceding embodiments, wherein the second compound comprises cyclohexanone, dialkyl ketone (preferably diethyl ketone or acetone), alkyl dione (preferably cyclohexanedione), levulinic acid, or a combination thereof.

Embodiment 11 is the method of any one of the preceding embodiments, wherein the second compound is not cyclopentanone.

Embodiment 12 is the method of any one of the preceding embodiments, wherein the second compound has an atomic weight of less than 1,000 Daltons, less than 500 Daltons, or less than 200 Daltons, or is an oligomer with a repeating unit having an atomic weight of less than 1,000 Daltons.

Embodiment 13 is the method of any one of the preceding embodiments, wherein the method comprises reacting with the third compound and optionally wherein the third compound comprises an epihalohydrin, preferably epichlorohydrin.

Embodiment 14 is the method of any one of the preceding embodiments, wherein the method comprises: reacting the first compound and the second compound in a first step resulting in an intermediate product (e.g., an aromatic diol such as a polyphenol, preferably a diphenol); and reacting the intermediate product with the third compound in a second step resulting in the monomer, optionally wherein the monomer comprises a polyepoxide monomer, preferably a diepoxide monomer.

Embodiment 15 is the method of any one of the preceding embodiments, wherein the method comprises: reacting the first compound and the third compound in a first step resulting in an intermediate product; and reacting the intermediate product with the second compound in a second step resulting in the monomer, optionally wherein the monomer comprises a polyepoxide monomer, preferably a diepoxide monomer.

Embodiment 16 is the method of any one of the preceding embodiments, wherein the first compound and the second compound are reacted at a ratio from 1.8:1 to 3:1 mole parts, from 1.8:1 to 2.5:1 mole parts, from 1.8:1 to 2.2:1 mole parts, or from 2:1 to 2.2:1 mole parts of the first compound and the second compound. In a preferred embodiment, the ratio of the first compound to the second compound is 2:1 or approximately 2:1 mol parts.

Embodiment 17 is the method of any one of the preceding embodiments, wherein the monomer is a diphenol or other aromatic diol.

Embodiment 18 is the method of any one of the preceding embodiments, wherein the monomer is of Formula (III):

Formula (III)

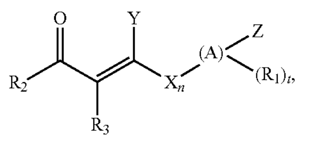

wherein A, $R_1$, X, Y, Z, n, and t are as in Formula (I) and $R_2$ and $R_3$ are as in Formula (II).

Embodiment 19 is the method of any one of the preceding embodiments, wherein the monomer is of Formula (IIIA):

Formula (IIIA)

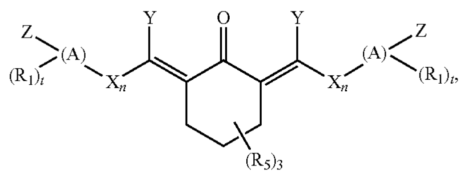

wherein A, $R_1$, X, Y, Z, n, and t are as in Formula (I) and each $R_5$ is independently selected from hydrogen or an organic group, preferably where $R_5$ is hydrogen.

Embodiment 20 is the method of any one of the preceding embodiments, wherein the monomer is of Formula (IIIB):

Formula (IIIB)

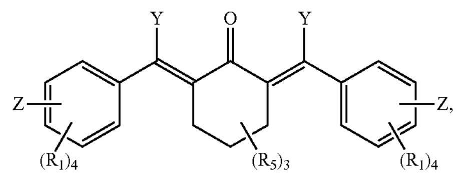

wherein $R_1$, Y, and Z are as in Formula (I) and $R_5$ is as in Formula (IIIA).

Embodiment 21 is the method of any one of the preceding embodiments, wherein the monomer is of Formula (IIIC):

Formula (IIIC)

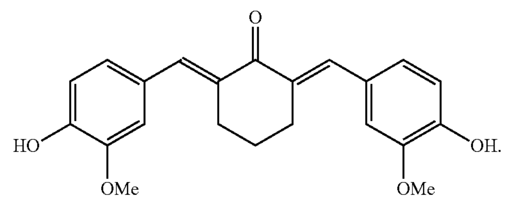

Embodiment 22 is the method of any one of the preceding embodiments, wherein the monomer is of Formula (IIID):

Formula (IIID)

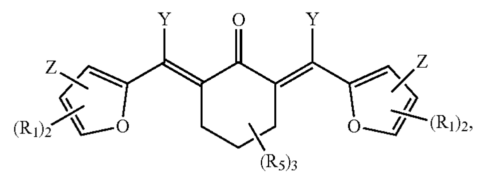

wherein $R_1$, Y, and Z are as in Formula (I) and $R_5$ is as in Formula (IIIA).

Embodiment 23 is the method of any of embodiments 18 to 22, wherein the depicted Z groups have been converted to epoxide-containing groups such that the monomer is a diepoxide.

Embodiment 24 is the method of any one of the preceding embodiments, wherein the monomer is of Formula (IIIE).

Formula (IIIE)

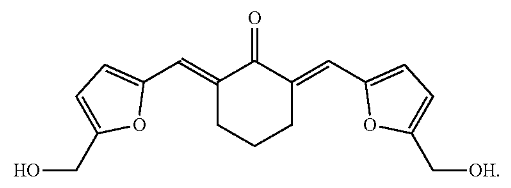

Embodiment 25 is the method of any one of the preceding embodiments, wherein the monomer is of Formula (IV):

Formula (IV)

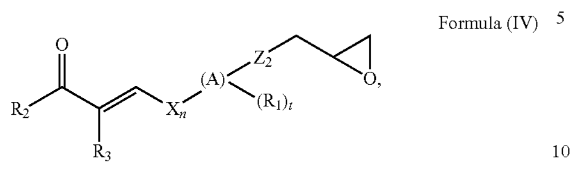

wherein A, $R_1$, X, Y, n, and t are as in Formula (I) and $R_2$ and $R_3$ are as in Formula (II), and wherein $Z_2$ is a residue of Z after reaction with epichlorohydrin, preferably wherein $Z_2$ is oxygen, —NH—, —$(CH_2)_m$O— where m is 1 or 2, or —COO—.

Embodiment 26 is the method of any one of the preceding embodiments, wherein the monomer is of Formula (IVA):

Formula (IVA)

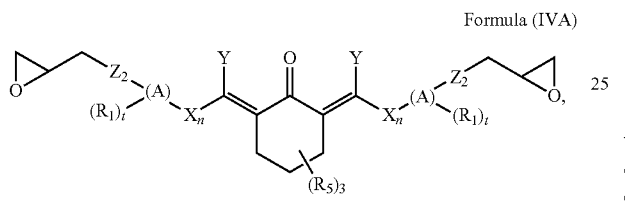

wherein A, $R_1$, X, Y, n, and t are as in Formula (I), $R_5$ is as in Formula (IIIA), and wherein $Z_2$ is as in Formula (IV).

Embodiment 27 is the method of any one of the preceding embodiments, wherein the monomer is of Formula (IVB):

Formula (IVB)

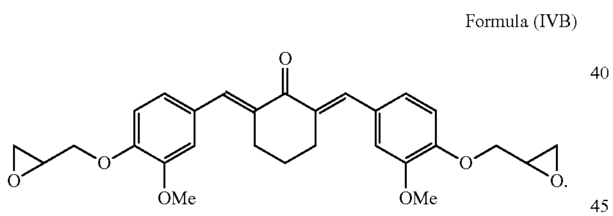

Embodiment 28 is the method of any one of the preceding embodiments, wherein the monomer is of Formula (IVC):

Formula (IVC)

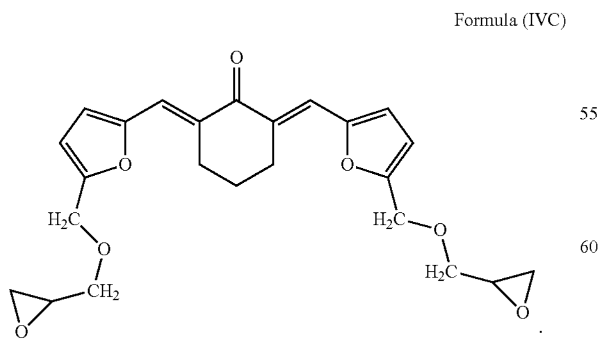

Embodiment 29 is the monomer resulting from the method of any one of the preceding embodiments.

Embodiment 30 is a monomer of Formula (III):

Formula (III)

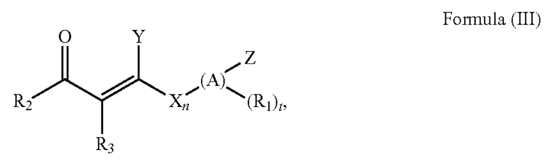

wherein A, $R_1$, X, Y, Z, n, and t are as in Formula (I) and $R_2$ and $R_3$ are as in Formula (II).

Embodiment 31 is a monomer of Formula (IIIA):

Formula (IIIA)

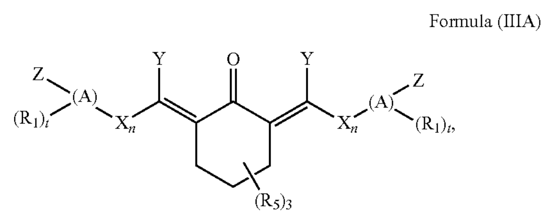

wherein A, $R_1$, X, Y, Z, n, and t are as in Formula (I) and each $R_5$ is independently selected from hydrogen or an organic group, preferably where $R_5$ is hydrogen.

Embodiment 32 is the monomer of embodiment 31, wherein the monomer is represented by Formula (IIIB):

Formula (IIIB)

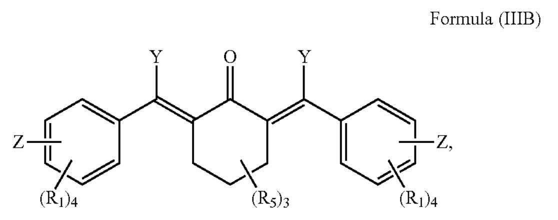

wherein $R_1$, Y, and Z are as in Formula (I) and $R_5$ is as in Formula (IIIA).

Embodiment 33 is the monomer of any one of embodiments 30 to 32, wherein the depicted Z groups have been converted to epoxide-containing groups such that the monomer is a diepoxide.

Embodiment 34 is the monomer of embodiment any one of embodiments 30 to 32, wherein the monomer is represented by Formula (IIIC):

Formula (IIIC)

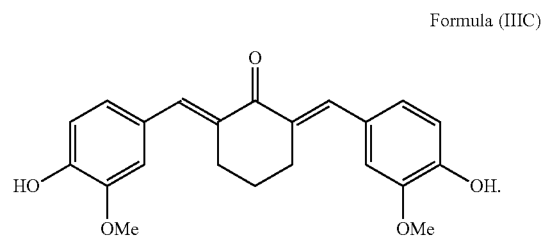 [SMILES: COc1cc(/C=C2\CCC/C(=C\c3ccc(O)c(OC)c3)C2=O)ccc1O]

Embodiment 35 is the monomer of embodiment 30 or 31, wherein the monomer is represented by Formula (IIID):

Formula (IIID)

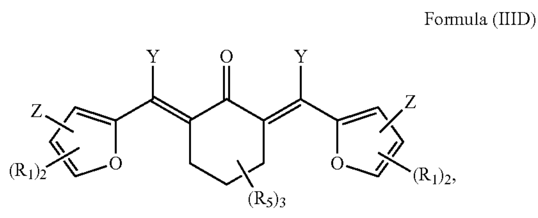

wherein $R_1$, Y, and Z are as in Formula (I) and $R_5$ is as in Formula (IIIA).

Embodiment 36 is the monomer of embodiment 35, wherein the monomer is represented by Formula (IIIE).

Formula (IIIE)

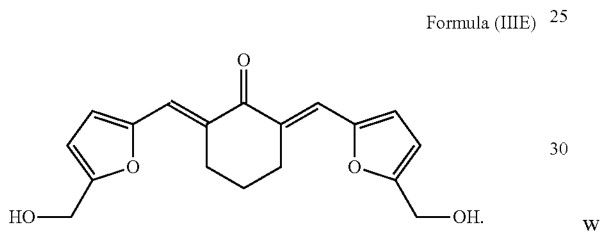

Embodiment 37 is a monomer of Formula (IV):

Formula (IV)

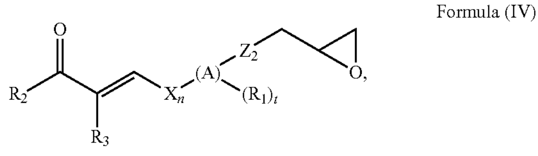

wherein A, $R_1$, X, Y, n, and t are as in Formula (I) and $R_2$ and $R_3$ are as in Formula (II), and wherein $Z_2$ is a residue of Z after reaction with epichlorohydrin, preferably wherein $Z_2$ is oxygen, —NH—, —$(CH_2)_m$O— where m is 1 or 2, or —COO—.

Embodiment 38 is the monomer of embodiment 37 represented by Formula (IVA):

Formula (IVA)

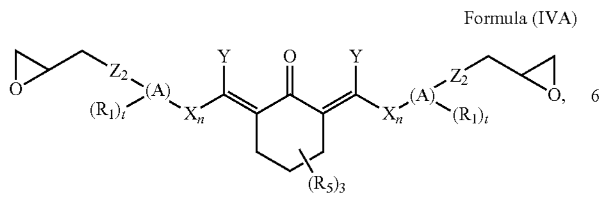

wherein A, $R_1$, X, Y, n, and t are as in Formula (I), $R_5$ is as in Formula (IIIA), and wherein $Z_2$ is as in Formula (IV).

Embodiment 39 is the monomer of embodiment 37 or 38, wherein the monomer is represented by Formula (IVB):

Formula (IVB)

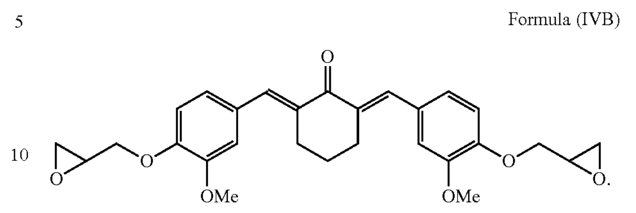

Embodiment 40 is the monomer of embodiment 37, wherein the monomer is represented by Formula (IVC):

Formula (IVC)

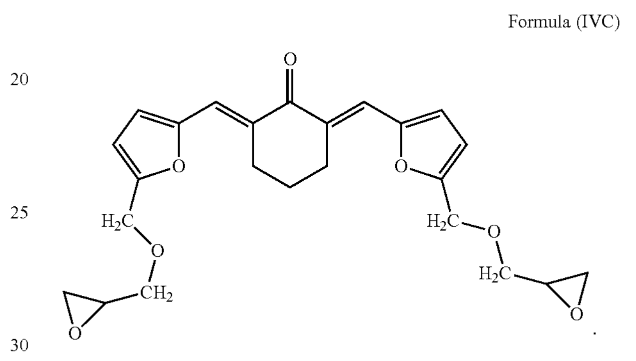

Embodiment 41 is the monomer of embodiment 37, wherein the monomer is represented by Formula (IVD):

Formula (IVD)

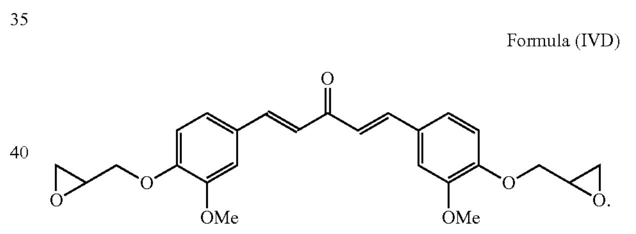

Embodiment 42 is a polymer comprising one or more segments derived from the monomer of any one of embodiments 30 to 41.

Embodiment 43 is the polymer of embodiment 42, wherein the polymer comprises a polyether polymer.

Embodiment 44 is the polymer of embodiment 42 or 43, wherein the polymer has a Tg of 30° C. or greater, 50° C. or greater, 60° C. or greater, 70° C. or greater, or 80° C. or greater.

Embodiment 45 is the polymer of any one of embodiment 42 to 44, wherein the polymer has a Tg of 150° C. or less, 130° C. or less, 120° C. or less, or 110° C. or less.

Embodiment 46 is the polymer of any one of embodiment 42 to 45, wherein the polymer has a number average molecular weight of 2000 or greater, 3000 or greater, 3500 or greater, or 4000 or greater.

Embodiment 47 is the polymer of any one of embodiments 42 to 46, wherein the polymer includes a plurality of secondary hydroxyl groups attached to a backbone of the polymer.

Embodiment 48 is the polymer of any one of embodiments 42 to 47, wherein the polymer includes one or more —$CH_2$—CH(OH)—$CH_2$— or —$CH_2$—$CH_2$—CH(OH)— backbone segments.

Embodiment 49 is the polymer of any one of embodiments 42 to 48, wherein the polymer has a polydispersity index (PDI) from about 1.5 to about 5, more preferably about 2 to about 3.5.

Embodiment 50 is the polymer of any one of embodiments 42 to 49, wherein the polymer comprises a polyether-acrylate copolymer, wherein one or more acrylic portions optionally includes carboxylic acid groups and/or salt groups thereof.

Embodiment 51 is the polymer of any one of embodiments 42 to 50, wherein the polymer includes water-dispersing groups (e.g., salt groups such as neutralized acid or neutralized base groups) and is water-dispersible.

Embodiment 52 is the polymer of any one of embodiments 42 to 51, wherein a backbone of the polymer includes (i) terminal oxirane end groups, (ii) terminal hydroxyl groups (e.g., hydroxyls of phenolic groups), or (iii) both (i) and (ii).

Embodiment 53 is the polymer of any one of embodiments 42 to 52, wherein the polymer is free of structural units derived from bisphenol A, bisphenol F, or bisphenol S.

Embodiment 54 is the polymer of any one of embodiments 42 to 53, wherein the polymer is free of structural units derived from a bisphenol (e.g., as in bisphenol A, bisphenol F, and bisphenol S).

Embodiment 55 is the polymer of any one of embodiments 42 to 54 comprising structural units derived from monomers, wherein the monomer of any one of embodiments 30 to 41 constitutes 5 wt-% or more, 10 wt-% or more, 20 wt-% or more, 35 wt-% or more, 50 wt-% or more, 65 wt-% or more, 80 wt-% or more, 90 wt-% or more, or 95 wt-% or more, or 99 wt-% or more; and 100 wt-% or less, 95 wt-% or less, 90 wt-% or less, 80 wt-% or less, 60 wt-% or less, 40 wt-% or less, 20 wt-% or less, or 10 wt-% or less of the monomers.

Embodiment 56 is the polymer of any one of embodiments 42 to 55 comprising one or more segments of the following formula:

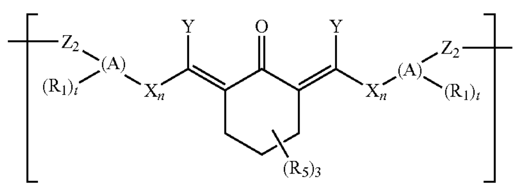

wherein A, $R_1$, X, Y, n, and t are as in Formula (I), $R_5$ is as in Formula (IIIA), and wherein $Z_2$ is oxygen, —NH—, —$(CH_2)_mO$— where m is 1 or 2, or —COO—.

Embodiment 57 is a coating or coating composition comprising the polymer of any one of embodiments 42 to 56.

Embodiment 58 is a coating composition comprising the polymer of any one of embodiments 42 to 56 and a solvent, the coating composition comprising 10 wt-% or more, wt-% or more, 20 wt-% or more, or 25 wt-% or more of non-volatile components; and no greater than 50 wt-% or no greater than 40 wt-% of non-volatile components.

Embodiment 59 is the coating composition of embodiment 58, wherein the solvent comprises at least 50 wt-%, at least 75 wt-%, at least 90 wt-%, or at least 95 wt-% of water, or wherein the solvent consists essentially of water.

Embodiment 60 is the coating composition of embodiment 58 or 59, wherein the polymer comprises salt groups, such as anionic or cationic salt groups, and preferably neutralized acid or base groups.

Embodiment 61 is the coating composition of any one of embodiments 58 to 60, wherein the polymer has an acid number of at least 40, at least 55, or at least 70 milligrams KOH per gram of the polymer.

Embodiment 62 is the coating composition of any one of embodiments 57 to 61, wherein the polymer of any one of embodiments 42 to 55 constitutes 5 wt-% or more, 10 wt-% or more, 20 wt-% or more, 35 wt-% or more, 50 wt-% or more, 65 wt-% or more, 80 wt-% or more, 90 wt-% or more, or 95 wt-% or more, or 99 wt-% or more of the coating composition, based on total weight of resin solids in the coating composition.

Embodiment 63 is the coating composition of any one of embodiments 57 to 62, wherein the polymer of any one of embodiments 42 to 56 constitutes 100 wt-% or less, 95 wt-% or less, 90 wt-% or less, 80 wt-% or less, 60 wt-% or less, 40 wt-% or less, 20 wt-% or less, 10 wt-% or less of the coating composition, based on total weight of resin solids in the coating composition.

Embodiment 64 is the coating composition of any one of embodiments 57 to 63, wherein the polymer has a polydispersity index ("PDI") of 1.5 or greater or 2 or greater; and/or 5 or less, or 3.5 or less; and/or wherein the PDI is from about 1.5 to about 5, more preferably from about 2 to about 3.5.

Embodiment 65 is the coating composition of any one of embodiments 57 to 64, wherein the polymer has a Tg of more than 0° C., at least 30° C., at least 40° C., at least 50° C., at least 60° C., or at least 70° C.; and/or less than 150° C., less than 130° C., or less than 110° C., as measured via differential scanning calorimetry ("DSC").

Embodiment 66 is the coating composition of any one of embodiments 57 to 65, wherein the coating composition further comprises one or more additives, and wherein the one or more additives comprise an adhesion promoter, a curing agent (e.g., crosslinker), a filler, a dye, a colorant, a toner, a coalescent, an extender, an anticorrosion agent, a flow control agent, a thixotropic agent, a dispersing agent, an antioxidant, an oxygen-scavenging material, an adhesion promoter, a light stabilizer, a catalyst, a lubricant, or a mixture thereof.

Embodiment 67 is a coating composition comprising the polymer of any one of embodiments 42 to 56, wherein the coating composition is provided as a powder coating.

Embodiment 68 is a food or beverage container comprising a coating made from the coating composition of any one of embodiments 57 to 67.

Embodiment 69 is the food or beverage container of embodiment 68 comprising a metal substrate, preferably aluminum, wherein the coating is disposed on at least a portion of the metal substrate.

Embodiment 70 is the food or beverage container of embodiment 68 or 69, wherein the coating has an average film thickness greater than 0.7 milligrams/square-inch (mg/inch$^2$), greater than 0.8 mg/inch$^2$, or greater than 0.9 mg/inch$^2$; and/or 5.5 mg/inch$^2$ or less, 4.0 mg/inch$^2$ or less, 3.0 mg/inch$^2$ or less, or 2.5 mg/inch$^2$ or less; and/or ranging from about 0.9 mg/inch$^2$ to about 1.1 mg/inch$^2$, from about 1.4 mg/inch$^2$ to about 1.6 mg/inch$^2$, or from about 1.9 mg/inch$^2$ to about 2.1 mg/inch$^2$.

Embodiment 71 is the food or beverage container of any one of embodiments 68 to 70, wherein the cured coating has a glass transition temperature of greater than 50° C., greater than 60° C., greater than 70° C., or greater than 80° C.;

and/or less than 120° C., less than 115° C., less than 110° C., or less than 100° C., as measured by differential scanning calorimetry (DSC).

Embodiment 72 is the food or beverage container of any one of embodiments 68 to 71, wherein the cured coating exhibits a global extraction of less than about 25 parts-per-million (ppm), more preferably less than about 10 ppm, and even more preferably less than about 1 ppm, pursuant to the Global Extraction test.

Embodiment 73 is a method comprising causing a polymer or coating composition of any of embodiments 42 to 67 to be used (e.g., as an interior or exterior coating) on a food or beverage container or a portion thereof.

Embodiment 74 is the method of embodiment 73, comprising curing at a curing temperature of greater than 150° C., greater than 165°, or greater than 180° C.; and/or less than 250° C., less than 240° C., or less than 230° C.

Embodiment 75 is the method of embodiment 74, wherein the curing has an oven residence time of 10 seconds to 30 minutes, or in some applications less than 1 minute, such as 10 seconds to 30 seconds, or more than 1 minute, such as from 1 minute to 2 minutes, or more than 5 minutes, such as from 10 to 30 minutes.

Embodiment 76 is the method of any one of embodiments 73 to 75, wherein the coating is applied by inside spray coating or coil coating.

Embodiment 77 is a multi-part epoxide system comprising: part A comprising the polyepoxide monomer of any one of embodiments 37 to 42; and part B comprising a hardener.

Embodiment 78 is a coating system or composite comprising a solution of: a monomer mixture comprising the monomer of any one of embodiments 30 to 42; and an unsaturated monomer, preferably (meth)acrylate or styrene.

Embodiment 79 is a coating system or composite obtained by free radical homopolymerization of an oligomer containing the monomer of any one of the embodiments to 42.

Embodiment 80 is a copolymer comprising a phenol pendant obtained by reacting: a compound comprising an aromatic ring and a carbonyl group; and a polymer containing a functional unit comprising a carbonyl group.

Embodiment 81 is the copolymer of embodiment 80, wherein the compound comprises vanillin, hydroxymethyl furfural, a hydroxybenzaldehyde (e.g., 4-hydroxybenzaldehyde or 2-hydroxybenzaldehyde), a hydroxyl naphthaldehyde (e.g., 1-hydroxy-2-naphthaldehyde, 3-hydroxy-2-naphthaldehyde, or 4-hydroxy-1-naphthaldehyde), 3-hydroxyacetophenone, a substituted variant thereof, or a combination thereof, preferably wherein the compound comprises vanillin or hydroxymethyl furfural.

Embodiment 82 is the copolymer of embodiment 80 or 81, wherein the polymer is an acrylic copolymer.

Embodiment 83 is the copolymer of any one of embodiments 80 to 82, wherein the functional unit comprises methacrolein, HMF methacrylate, or vanillin methacrylate.

Embodiment 84 is the method of any one of embodiments 1 to 24, wherein the monomer is free of epoxide groups.

Embodiment 85 is the method of any one of embodiments 1 to 24 further comprising reacting the monomer with polycyclocarbonate, preferably dicyclocarbonate, to form a polyether polymer.

Embodiment 86 is the method of embodiment 82, wherein the polycyclocarbonate comprises diglyceroldicyclocarbonate, (glycerolcyclocarbonate) dicarbonate, or a combination thereof.

Embodiment 87 is the monomer of any one of embodiments 29 to 36, wherein the monomer is free of epoxide groups.

Embodiment 88 is the polymer of any one of embodiments 42 to 56, wherein the polymer is free of epoxide groups.

Embodiment 89 is the polymer of embodiment 88, wherein the polymer comprises structural units derived from polycyclocarbonate, preferably dicyclocarbonate.

Embodiment 90 is the polymer of embodiment 89, wherein the polycyclocarbonate comprises diglyceroldicyclocarbonate, (glycerolcyclocarbonate) dicarbonate, or a combination thereof.

Embodiment 91 is the coating composition of any one of embodiments 57 to 67, wherein the polymer is free of epoxide groups.

Embodiment 92 is the coating composition of embodiment 91, wherein the polymer comprises structural units derived from polycyclocarbonate, preferably dicyclocarbonate.

Embodiment 93 is the coating composition of embodiment 92, wherein the polycyclocarbonate comprises diglyceroldicyclocarbonate, (glycerolcyclocarbonate) dicarbonate, or a combination thereof.

Embodiment 94 is the food or beverage container of any one of embodiments 69 to 72, wherein the polymer is free of epoxide groups.

Embodiment 95 is the food or beverage container of embodiment 94, wherein the polymer comprises structural units derived from polycyclocarbonate, preferably dicyclocarbonate.

Embodiment 96 is the food or beverage container of embodiment 95, wherein the polycyclocarbonate comprises diglyceroldicyclocarbonate, (glycerolcyclocarbonate) dicarbonate, or a combination thereof.

Embodiment 97 is the method of any one of embodiments 73 to 76, wherein the polymer is free of epoxide groups.

Embodiment 98 is the method of embodiment 97, wherein the polymer comprises structural units derived from polycyclocarbonate, preferably dicyclocarbonate.

Embodiment 99 is the method of embodiment 98, wherein the polycyclocarbonate comprises diglyceroldicyclocarbonate, (glycerolcyclocarbonate) dicarbonate, or a combination thereof.

Embodiment 100 is the copolymer of any one of embodiments 80 to 83, wherein the compound is free of epoxide groups.

Embodiment 101 is the copolymer of embodiment 100, wherein the compound comprises one or more structural units derived from polycyclocarbonate, preferably dicyclocarbonate.

Embodiment 102 is the copolymer of embodiment 101, wherein the polycyclocarbonate comprises diglyceroldicyclocarbonate, (glycerolcyclocarbonate) dicarbonate, or a combination thereof.

In some embodiments, a method of forming a monomer comprises reacting reactants comprising a first compound comprising an aromatic ring and a carbonyl group; a second compound comprising a carbonyl group; and optionally a third compound comprising an epoxide ring; wherein the monomer comprises a polyol (e.g., a polyphenol) or a polyepoxide. The first compound may comprise an alkoxide group directly attached to the aromatic ring. The first compound may comprise a hydroxy group, which is preferably directly attached to the aromatic ring. The carbonyl group of the first compound may comprise an acyl group, preferably —CH(=O) or an acetyl group, which is preferably directly attached to the aromatic ring. The first compound may be of Formula (I) or (IA) as described hereinabove. The first compound may comprise vanillin, hydroxymethyl furfural, a hydroxybenzaldehyde (e.g., 4-hydroxybenzaldehyde or 2-hydroxybenzaldehyde), a hydroxyl naphthaldehyde (e.g., 1-hydroxy-2-naphthaldehyde, 3-hydroxy-2-naphthaldehyde, or 4-hydroxy-1-naphthaldehyde), 3-hydroxyacetophenone, a substituted variant thereof, or a combination thereof, preferably wherein the first compound may comprise vanillin or hydroxymethyl furfural. The second compound may be of Formula (II) as described hereinabove. The second compound may comprise cyclohexanone, dialkyl ketone (preferably diethyl ketone or acetone), alkyl dione (preferably cyclohexanedione), levulinic acid, or a combination thereof. The method may comprise reacting with the third compound and wherein the third compound may comprise an epihalohydrin, preferably epichlorohydrin. The method may comprise: reacting the first compound and the second compound in a first step resulting in an intermediate product (e.g., an aromatic diol such as a polyphenol, preferably a diphenol); and reacting the intermediate product with the third compound in a second step resulting in the monomer, wherein the monomer may comprise a polyepoxide monomer, preferably a diepoxide monomer. The method may comprise: reacting the first compound and the third compound in a first step resulting in an intermediate product; and reacting the intermediate product with the second compound in a second step resulting in the monomer, wherein the monomer may comprise a polyepoxide monomer, preferably a diepoxide monomer. The first compound and the second compound may be reacted at a ratio from 1.8:1 to 3:1 mole parts, from 1.8:1 to 2.5:1 mole parts, from 1.8:1 to 2.2:1 mole parts, or from 2:1 to 2.2:1 mole parts of the first compound and the second compound. In a preferred embodiment, the ratio of the first compound to the second compound may be 2:1 or approximately 2:1 mol parts. The monomer is a diphenol or other aromatic diol. The monomer may be of Formula (III) as described hereinabove. The monomer may be of Formula (IIIA) as described hereinabove. The monomer may be of Formula (IIIB) as described hereinabove. The monomer may be of Formula (IIIC) as described hereinabove. The monomer may be of Formula (IIID) as described hereinabove. The monomer may be of Formula (IIIE) as described hereinabove. The monomer may be of Formula (IV) as described hereinabove. The monomer may be of Formula (IVA) as described hereinabove. The monomer may be of Formula (IVB) as described hereinabove. The monomer may be of Formula (IVC) as described hereinabove.

In some embodiments, a polymer comprises one or more segments derived from the monomer of Formula (III) as described hereinabove, or one or more segments derived from the monomer of Formula (IIIA) as described hereinabove, or one or more segments derived from the monomer of Formula (TIM) as described hereinabove, or one or more segments derived from the monomer of Formula (IIIC) as described hereinabove, or one or more segments derived from the monomer of Formula (IIID) as described hereinabove, or one or more segments derived from the monomer of Formula (IIIE) as described hereinabove, or one or more segments derived from the monomer of Formula (IV) as described hereinabove, or one or more segments derived from the monomer of Formula (IVA) as described hereinabove, or one or more segments derived from the monomer of Formula (IVB) as described hereinabove, or one or more segments derived from the monomer of Formula (IVC) as described hereinabove. The polymer may comprise a polyether polymer. The polymer may have a Tg of 30° C. or greater, 50° C. or greater, 60° C. or greater, 70° C. or greater, or 80° C. or greater. The polymer may have a Tg of 150° C. or less, 130° C. or less, 120° C. or less, or 110° C. or less. The polymer may have a number average molecular weight of 2000 or greater, 3000 or greater, 3500 or greater, or 4000 or greater. The polymer includes a plurality of secondary hydroxyl groups attached to a backbone of the polymer. The polymer includes one or more $—CH_2—CH(OH)—CH_2—$ or $—CH_2—CH_2—CH(OH)—$ backbone segments. The polymer may have a polydispersity index (PDI) from about 1.5 to about 5, more preferably about 2 to about 3.5. The polymer may comprise a polyether-acrylate copolymer, wherein one or more acrylic portions optionally includes carboxylic acid groups and/or salt groups thereof. The polymer includes water-dispersing groups (e.g., salt groups such as neutralized acid or neutralized base groups) and may be water-dispersible. A backbone of the polymer may include (i) terminal oxirane end groups, (ii) terminal hydroxyl groups (e.g., hydroxyls of phenolic groups), or (iii) both (i) and (ii). The polymer may be free of structural units derived from bisphenol A, bisphenol F, or bisphenol S. The polymer may be free of structural units derived from a bisphenol (e.g., as in bisphenol A, bisphenol F, and bisphenol S). The polymer may comprise structural units derived from the monomers, wherein the monomer may constitutes wt-% or more, 10 wt-% or more, 20 wt-% or more, 35 wt-% or more, 50 wt-% or more, 65 wt-% or more, 80 wt-% or more, 90 wt-% or more, or 95 wt-% or more, or 99 wt-% or more; and 100 wt-% or less, 95 wt-% or less, 90 wt-% or less, 80 wt-% or less, 60 wt-% or less, 40 wt-% or less, 20 wt-% or less, or 10 wt-% or less of the monomers.

In some embodiments, a coating or coating composition comprises the polymer comprising one or more segments derived from the monomer of Formula (III) as described hereinabove, or one or more segments derived from the monomer of Formula (IIIA) as described hereinabove, or one or more segments derived from the monomer of Formula (IIIB) as described hereinabove, or one or more segments derived from the monomer of Formula (IIIC) as described hereinabove, or one or more segments derived from the monomer of Formula (IIID) as described hereinabove, or one or more segments derived from the monomer of Formula (IIIE) as described hereinabove, or one or more segments derived from the monomer of Formula (IV) as described hereinabove, or one or more segments derived from the monomer of Formula (IVA) as described hereinabove, or one or more segments derived from the monomer of Formula (IVB) as described hereinabove, or one or more segments derived from the monomer of Formula (IVC) as described hereinabove. The coating composition may comprise the polymer and a solvent, the coating composition comprising 10 wt-% or more, 15 wt-% or more, 20 wt-% or more, or 25 wt-% or more of non-volatile components; and no greater than 50 wt-% or no greater than 40 wt-% of non-volatile components. The solvent may comprise at least 50 wt-%, at least 75 wt-%, at least 90 wt-%, or at least 95 wt-% of water, or wherein the solvent consists essentially of water. The polymer may comprise salt groups, such as anionic or cationic salt groups, and preferably neutralized acid or base groups. The polymer may have an acid number of at least 40, at least or at least 70 milligrams KOH per gram of the polymer. The polymer may constitutes wt-% or more, 10 wt-% or more, 20 wt-% or more, 35 wt-% or more, 50 wt-% or more, 65 wt-% or more, 80 wt-% or more, 90 wt-% or more, or 95 wt-% or more, or 99 wt-% or more of the coating composition, based on total weight of resin solids in the coating composition. The polymer may constitute 100 wt-% or less, 95 wt-% or less, 90 wt-% or less, 80 wt-% or less, wt-% or less, 40 wt-% or less, 20 wt-% or less, 10 wt-% or less of the coating composition, based on total weight of resin solids in the coating composition. The polymer may have a polydispersity index ("PDI") of 1.5 or greater or 2 or greater; and/or 5 or less, or 3.5 or less; and/or wherein the PDI may be from about 1.5 to about 5, more preferably from about 2 to about 3.5. The polymer may have a Tg of more than 0° C., at least 30° C., at least 40° C., at least 50° C., at least 60° C., or at least 70° C.; and/or less than 150° C., less than 130° C., or less than 110° C., as measured via differential scanning calorimetry ("DSC"). The coating composition further may comprise one or more additives, and wherein the one or more additives comprise an adhesion promoter, a curing agent (e.g., crosslinker), a filler, a dye, a colorant, a toner, a coalescent, an extender, an anticorrosion agent, a flow control agent, a thixotropic agent, a dispersing agent, an antioxidant, an oxygen-scavenging material, an adhesion promoter, a light stabilizer, a catalyst, a lubricant, or a mixture thereof. The coating composition may be provided as a powder coating. In some embodiments, a food or beverage container may comprise a coating made from the coating composition. The food or beverage container may comprise a metal substrate, preferably aluminum, wherein the coating may be disposed on at least a portion of the metal substrate. The coating may have an average film thickness greater than 0.7 milligrams/square-inch (mg/inch$^2$), greater than 0.8 mg/inch$^2$, or greater than 0.9 mg/inch$^2$; and/or 5.5 mg/inch$^2$ or less, 4.0 mg/inch$^2$ or less, 3.0 mg/inch$^2$ or less, or 2.5 mg/inch$^2$ or less; and/or ranging from about 0.9 mg/inch$^2$ to about 1.1 mg/inch$^2$, from about 1.4 mg/inch$^2$ to about 1.6 mg/inch$^2$, or from about 1.9 mg/inch$^2$ to about 2.1 mg/inch$^2$. The cured coating may have a glass transition temperature of greater than 50° C., greater than 60° C., greater than 70° C., or greater than 80° C.; and/or less than 120° C., less than 115° C., less than 110° C., or less than 100° C., as measured by differential scanning calorimetry (DSC). The cured coating exhibits a global extraction of less than about 25 parts-per-million (ppm), more preferably less than about 10 ppm, and even more preferably less than about 1 ppm, pursuant to the Global Extraction test. In some embodiments, a method may comprise causing the polymer or coating composition to be used (e.g., as an interior or exterior coating) on a food or beverage container or a portion thereof. The method may comprise curing at a curing temperature of greater than 150° C., greater than 165°, or greater than 180° C.; and/or less than 250° C., less than 240° C., or less than 230° C. The curing may have an oven residence time of 10 seconds to 30 minutes, or in some applications less than 1 minute, such as 10 seconds to 30 seconds, or more than 1 minute, such as from 1 minute to 2 minutes, or more than 5 minutes, such as from 10 to 30 minutes. The coating may be applied by inside spray coating or coil coating.

EXAMPLES

Example 1A

In Example 1A, a diphenol monomer was prepared from vanillin and cyclohexanone.

In a glass vessel, 4.3 g (0.044 mol) of cyclohexanone, 13.66 g (0.09 mol) of vanillin, and 80 mL of ethanol were mixed. The mixture was stirred at room temperature while adding dropwise 89 g (0.864 mol) of HCl 35%. After addition of HCl, the mixture was maintained at room temperature for 40 h. One liter of demineralized water was added. The precipitate was washed with 500 mL of water and dried at 80° C. The precipitate was identified as 2,6 di(6-hydroxy, 5-methoxy)benzylidene cyclohexanone by NMR. The NMR spectrum is shown in FIG. 1A.

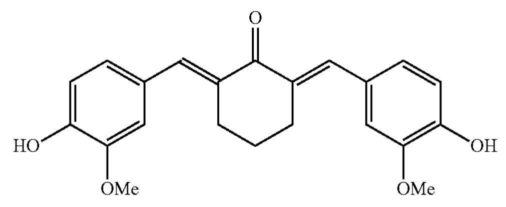 [SMILES: COc1cc(/C=C2\CCC/C(=C\c3ccc(O)c(OC)c3)C2=O)ccc1O]

2,6 di(6-hydroxy, 5-methoxy)benzylidene cyclohexanone

The yield of the resulting diphenol can be calculated as a percentage of a theoretical yield. In theory, two moles of vanillin (having a molecular weight of 152.1 g/mol) and one mole of cyclohexanone (having a molecular weight of 98.1 g/mol) produces one mole of 2,6 di(6-hydroxy, 5-methoxy) benzylidene cyclohexanone (having a molecular weight of 366.4 g/mol). Thus, in theory, 4.3 g cyclohexanone and 13.66 g vanillin produce 14.7 g of 2,6 di(6-hydroxy, 5-methoxy)benzylidene cyclohexanone. The calculated yield achieved in this example was 12.6 g/14.7 g=86%.

Example 1B

In Example 1B, a diglycidyl ether ("DGE") was prepared from the diphenol of Example 1A and epichlorohydrin.

Figure 1B:
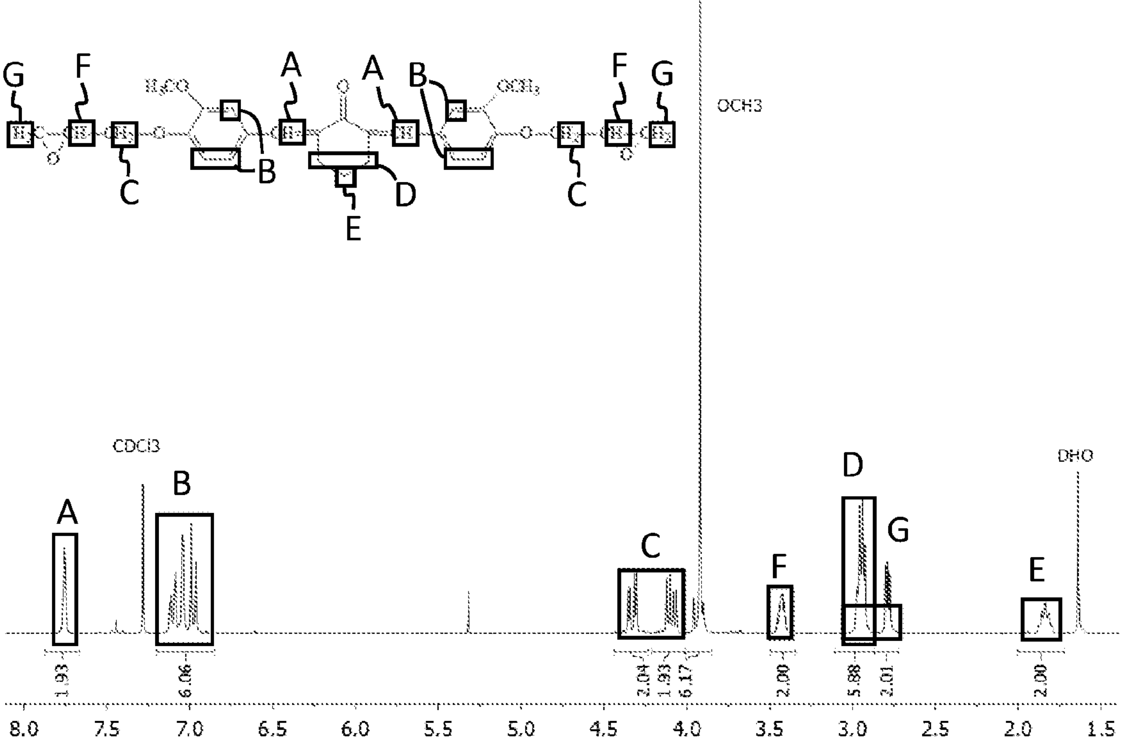
FIG. 1B is an NMR spectrum of the compound prepared in Example 1B.

A glass vessel was loaded with 3 g (8.19 mmol) of the diphenol of Example 1A, g (0.82 mmol) benzyl triethyl ammonium chloride ("TEBAC"), 7.57 g (81.9 mmol) epichlorohydrin, and 30 mL tetrahydrofuran ("THF"). The mixture was stirred at room temperature until the components were completely dissolved. Then, a NaOH solution (4.9 g NaOH in 9.8 g water) was added at 15° C. The mixture was stirred for 15 hours at room temperature. 30 mL of deionized ("DI") water and 120 mL of dichloromethane were added. After decantation, the organic phase was washed with 30 mL water saturated with NaCl. The solution was dried over $Na_2SO_4$. After drying, the solution was filtered and the solvent was removed by distillation under reduced pressure at 70° C. The resulting yellow powder was identified as the diglycidyl ether by NMR. The NMR spectrum is shown in FIG. 1B. The calculated yield was 94%.

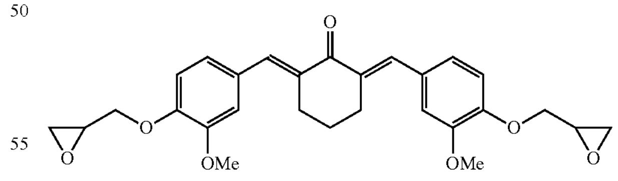

Diglycidyl ether of 2,6 di(6-hydroxy, 5-methoxy)benzylidene cyclohexanone

Example 2A

In Example 2A, vanillin was epoxidized with epichlorohydrin.

Figure 2A:
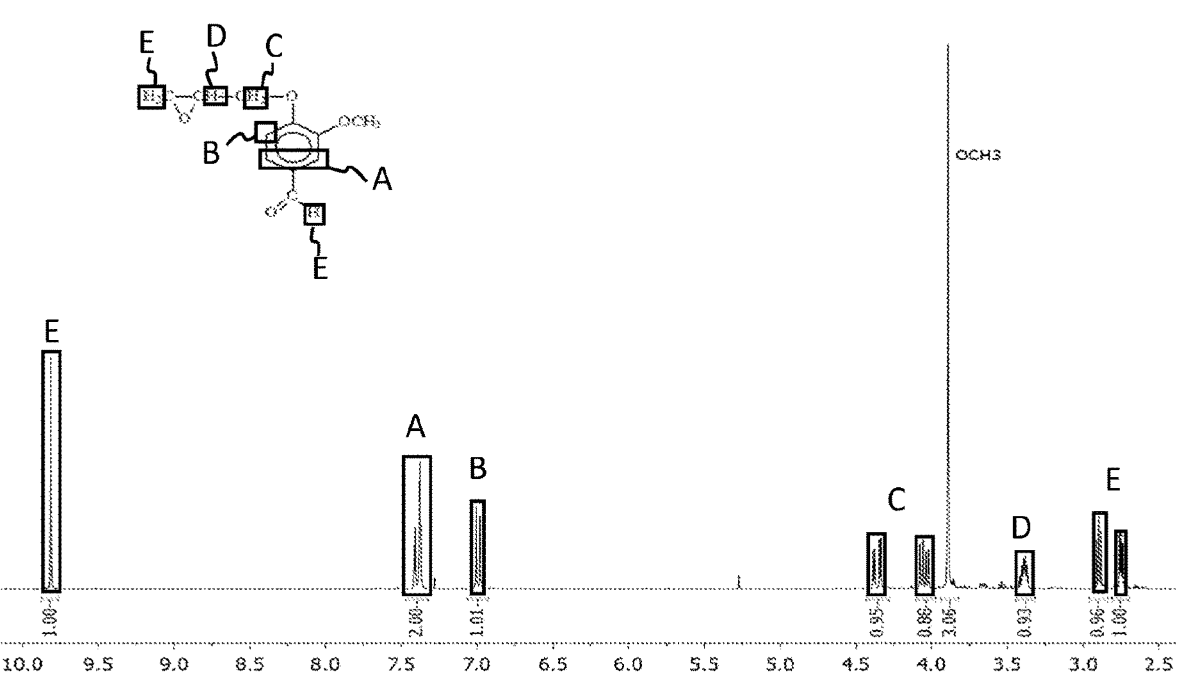
FIG. 2A is an NMR spectrum of the compound prepared in Example 2A.

100 g (0.66 mol) of vanillin was dissolved in 486.87 g (5.62 mol) of epichlorohydrin and 23 g of tetraethyl ammonium ("TEA") at 70° C. After 4 h at 70° C., dichloromethane was added. Then the mixture was washed twice with DI water and dried over $Na_2SO_4$. After drying, the solvent and the unreacted epichlorohydrin were removed by distillation under vacuum (0.01 bar). After drying, 136.8 g of a beige powder was obtained. This powder was dissolved in 100 g dichloromethane, 26.3 g NaOH in solution in 104.4 g water, and 6.9 g tetraethyl ammonium bromide. The mixture was left for 3 hours at room temperature. Another 200 g dichloromethane was added and the mixture was washed with water. The organic phase was dried with $Na_2SO_4$. The solvent was removed by distillation under vacuum (0.01 bar) at 70° C. After drying in the oven, 130 g of a beige produce was obtained and was identified as the monoglycidyl ether of vanillin by NMR. The NMR spectrum is shown in FIG. 2A. The calculated yield was 95%.

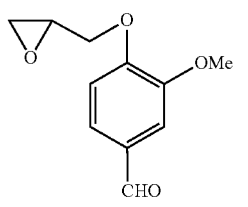 [SMILES: COc1cc(C=O)ccc1OCC1CO1]

Monoglycidyl Ether of Vanillin

Example 2B

In Example 2B, a diepoxide monomer was prepared from the monoglycidyl ether of vanillin of Example 2A and acetone.

Figure 2B:
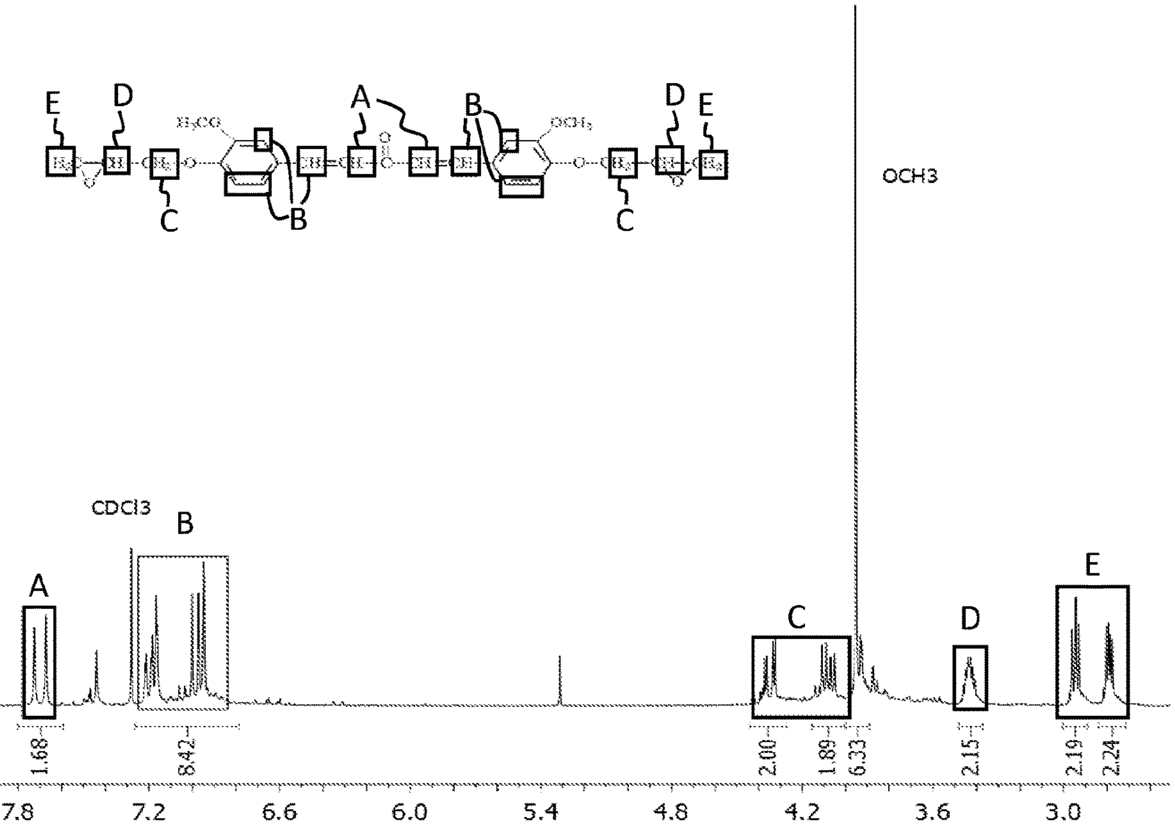
FIG. 2B is an NMR spectrum of the compound prepared in Example 2B.

14.3 g (0.069 mol) of vanillin monoglycidyl ether was dissolved in 2 g (0.034 mol) acetone and 55 g THF. NaOH solution (3.2 g NaOH in 31.7 g of water) was added. The mixture was stirred for 8 hours at room temperature. The THF was removed by distillation under vacuum (0.01 bar) at 70° C. 50 g of water was added to precipitate the produce. After filtration, washing with water, and drying in the oven (50° C.), 12.8 g of an orange solid was obtained. The produce was identified as a diepoxide by NMR. The NMR spectrum is shown in FIG. 2B. The calculated yield was 85%.

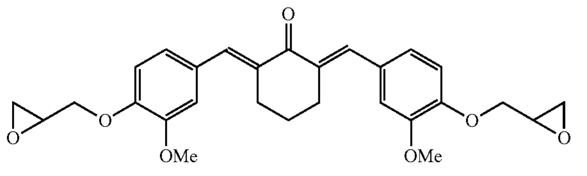 [SMILES: COc1cc(/C=C2\CCC/C(=C\c3ccc(OCC4CO4)c(OC)c3)C2=O)ccc1OCC1CO1]

Diglycidyl ether of 1,3 di(6-hydroxy, 5-methoxy)benzylidene 2-propanone

Example 3A

In Example 3A, an aromatic diol monomer was prepared from hydroxymethyl furfural ("HMF") and cyclohexanone.

In a glass vessel, 5 g (0.051 mol) of cyclohexanone, 13.17 g (0.104 mol) HMF, and 50 mL ethanol were mixed. Under stirring at room temperature, 15.5 g (0.112 mol) of $K_2CO_3$ in 62 mL of water was added dropwise. The mixture was stirred for 24 h at room temperature. The mixture was filtered and washed with 100 mL water. The resulting yellow powder was dried in the oven at 80° C., resulting in 15.5 g of the product. The product was identified by NMR as the aromatic diol adduct of HMF and cyclohexanone:

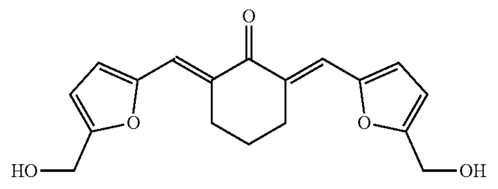 [SMILES: O=C1/C(=C/c2ccc(CO)o2)CCC/C1=C\c1ccc(CO)o1]

Figure 3A:
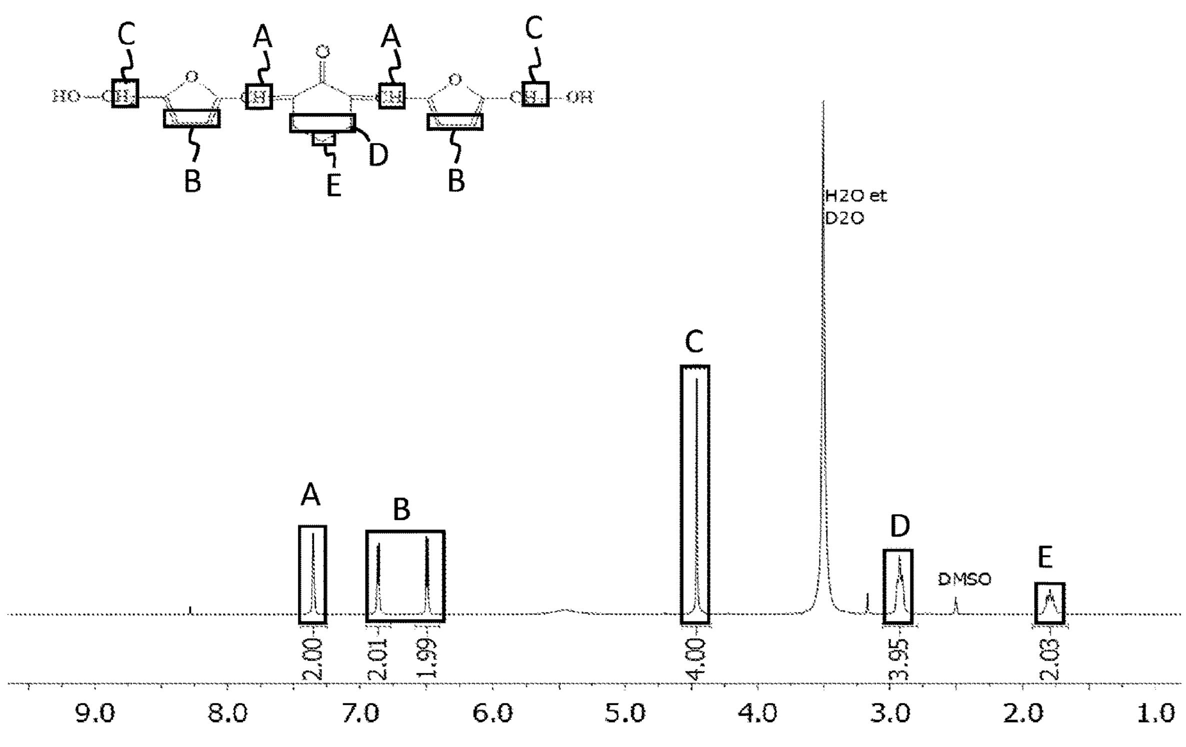
FIG. 3A is an NMR spectrum of the compound prepared in Example 3A.

The NMR spectrum is shown in FIG. 3A. The calculated yield was 97%.

Example 3B

In Example 3B, a diglycidyl ether ("DGE") was prepared from the aromatic diol of Example 3A and epichlorohydrin.

A glass vessel was loaded with 2.5 g (8 mmol) of the diphenol of Example 3A, 0.18 g (0.8 mmol) TEBAC, 7.36 g (80 mmol) epichlorohydrin, and 15 g THF. The mixture was stirred at room temperature until the mixture was homogenous. Then, a NaOH solution (4.77 g NaOH in 9.54 g water) was added and the mixture was stirred for 16 hours at room temperature. 30 mL of deionized ("DI") water and 100 mL of dichloromethane were added. The organic phase was washed with water. The solution was dried over $Na_2SO_4$. After drying, the solution was filtered and the organic solvent and excess epichlorohydrin were removed by distillation under vacuum (0.01 bar) at 70° C. 3 g of brown viscous liquid was obtained and was identified as the diglycidyl ether by NMR.

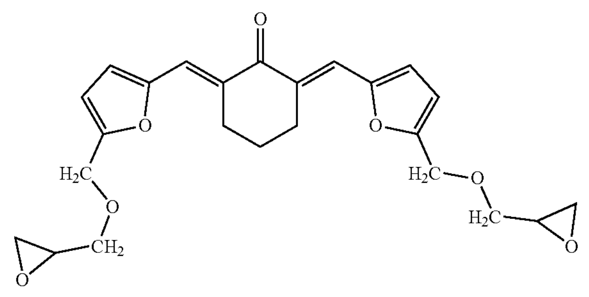 [SMILES: O=C1/C(=C/c2ccc(COCC3CO3)o2)CCC/C1=C\c1ccc(COCC2CO2)o1]

Diglycidyl Ether of the Diol Adduct of HMF and Cyclohexanone

Figure 3B:
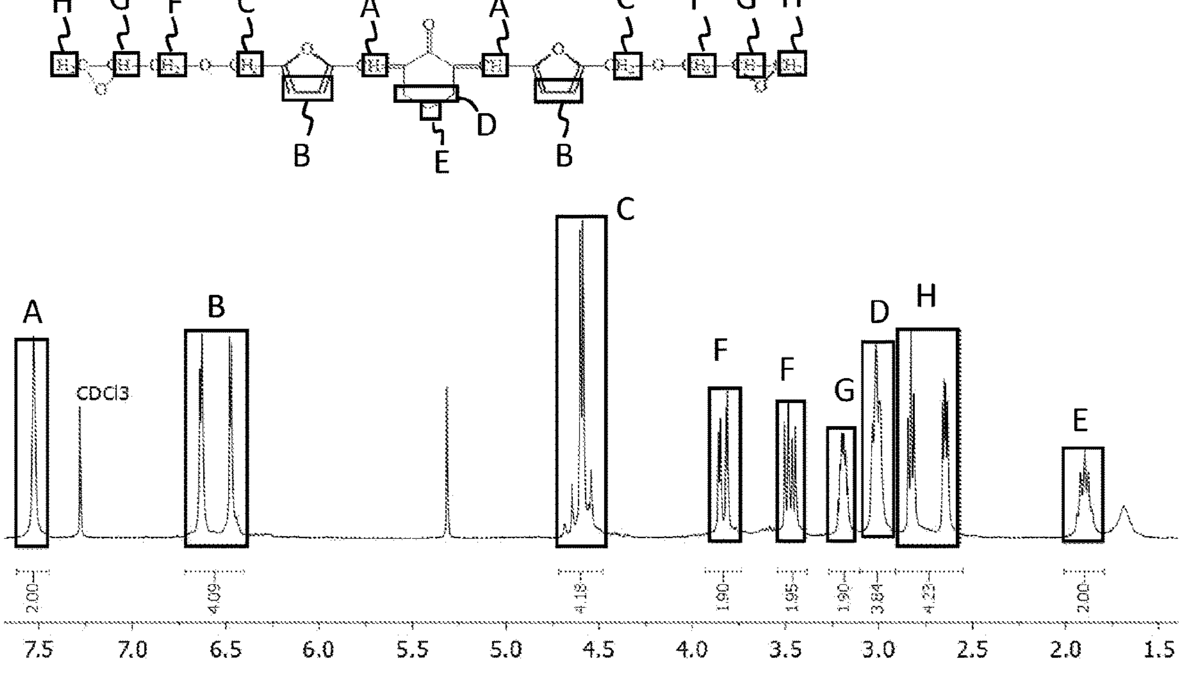
FIG. 3B is an NMR spectrum of the compound prepared in Example 3B.

The NMR spectrum is shown in FIG. 3B. The calculated yield was 90%.

Example 4A

In Example 4A, HMF was epoxidized with epichlorohydrin.

A glass vessel equipped with a condenser, a stirrer, and a temperature probe was loaded with 10 g (0.079 mol) HMF, 0.9 g (0.004 mol) TEBAC, 36.68 g (0.396 mol) epichlorohydrin, and 12.05 g (0.087 mol) $K_2CO_3$. The mixture was stirred for 48 hours at 70° C. 30 mL dichloromethane and 20 mL water were added. After separation, the organic phase was washed with 10 mL water and dried over $Na_2SO_4$. After drying, the dichloromethane and the unreacted epichlorohydrin were removed by distillation under vacuum (0.01 bar).

Figures 4, 5:
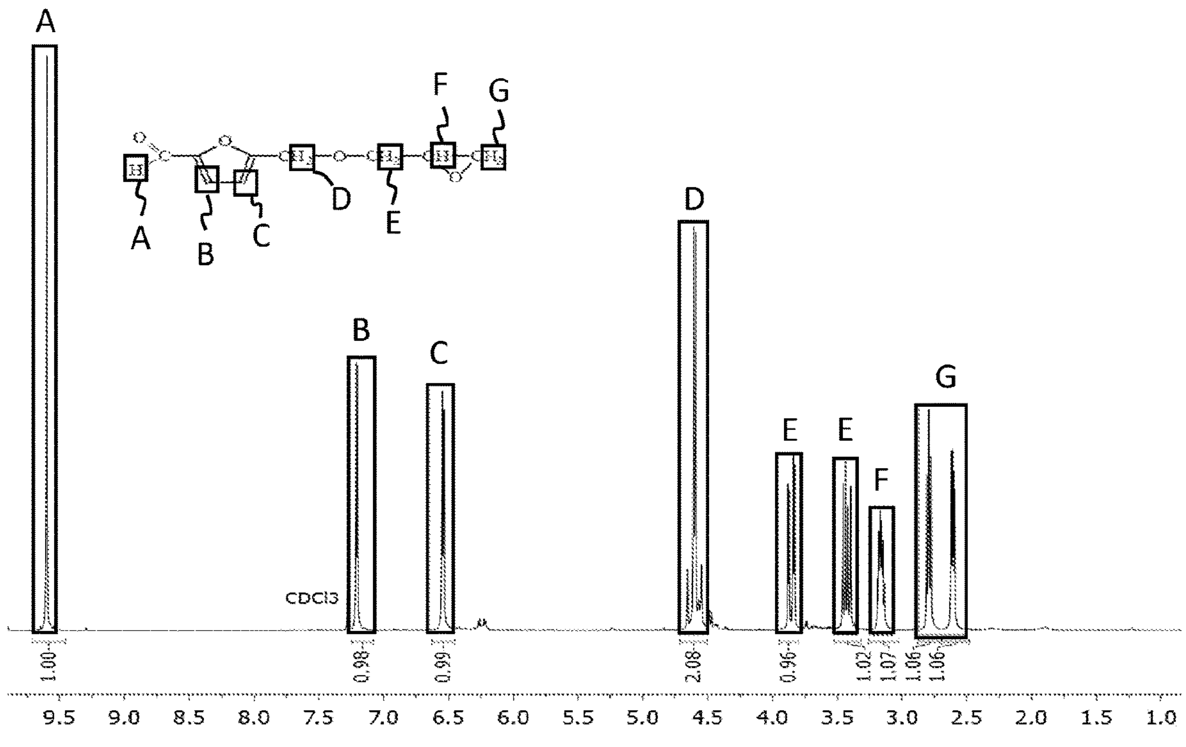
FIG. 4 is an NMR spectrum of the compound prepared in Example 4A.
FIG. 5 is an NMR spectrum of the compound prepared in Example 5.

The residue was loaded in a glass vessel equipped with a condenser, a stirrer, and a temperature probe with 10 mL dichloromethane. Under stirring, a solution of 3.49 g NaOH, 0.92 g tetraethyl ammonium bromide, and 13.85 g of water was added. The mixture was stirred at room temperature for 3 hours. 30 mL dichloromethane and 20 mL water were added. After separation, the organic phase was washed with 10 mL water and dried over $Na_2SO_4$. After drying, the dichloromethane and the unreacted epichlorohydrin were removed by distillation under vacuum (0.01 bar). The product was identified by NMR as the monoglycidyl ether of HMF. The NMR spectrum is shown in FIG. 4.

Example 4B

In Example 4B, a diepoxide monomer was prepared from the monoglycidyl ether of HMF of Example 4A and cyclohexanone.

A glass vessel was loaded with 2 g (0.02 mol) of cyclohexanone, 7.79 g (0.043 mol) of HMF glycidyl ether, and 15 mL ethanol. The mixture was stirred at room temperature while adding dropwise a NaOH solution (1.9 g (0.047 mol) NaOH in 18.4 mL water). The mixture was stirred for 24 hours at room temperature. 30 mL of water and 100 mL of dichloromethane were added. The organic phase was washed with water twice. The organic phase was dried over $Na_2SO_4$. After drying, the solution was filtered and the organic solvent and excess epichlorohydrin were removed by distillation under vacuum (0.01 bar) at 70° C. 6.8 g of a viscous liquid was obtained. The compound was identified as cyclohexanone 2,6 methylene bis (2-furan, 5-methanol glycidyl ether) by NMR, similar to Example 3B.

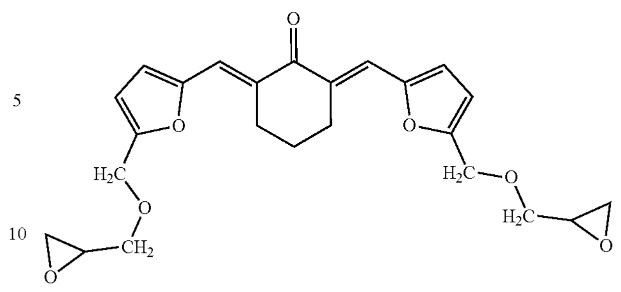

Diglycidyl Ether of the Diphenol Adduct of HMF and Cyclohexanone

Example 5

In Example 5, a polyether polymer was prepared from the vanillin-derived diphenol of Example 1A and the vanillin-derived diglycidyl ether of Example 1B.

1.72 g (0.0047 mol) of the vanillin-derived diphenol (2,6 di(6-hydroxy, 5-methoxy)benzylidene cyclohexanone) and 3 g (0.0063 mol) of its DGE (diglycidyl ether of 2,6 di(6-hydroxy, 5-methoxy)benzylidene cyclohexanone) were dissolved in 8 g DMSO at 180° C. When the mixture was homogeneous, 14.2 mg of butyl triphenyl phosphonium bromide was added and the mixture was maintained at 180° C. for 4 h. It was observed that the viscosity of the mixture significantly increased. The reaction product was observed in an NMR spectrum, showing the adduct of the vanillin diphenol and its DGE. The NMR spectrum is shown in FIG. 5.

Example 6

In Example 6, a polyether polymer was prepared from the DGE of the diphenol adduct of HMF and cyclohexanone of Example 4B and methoxy hydroquinone. The preparation is represented by the following reaction:

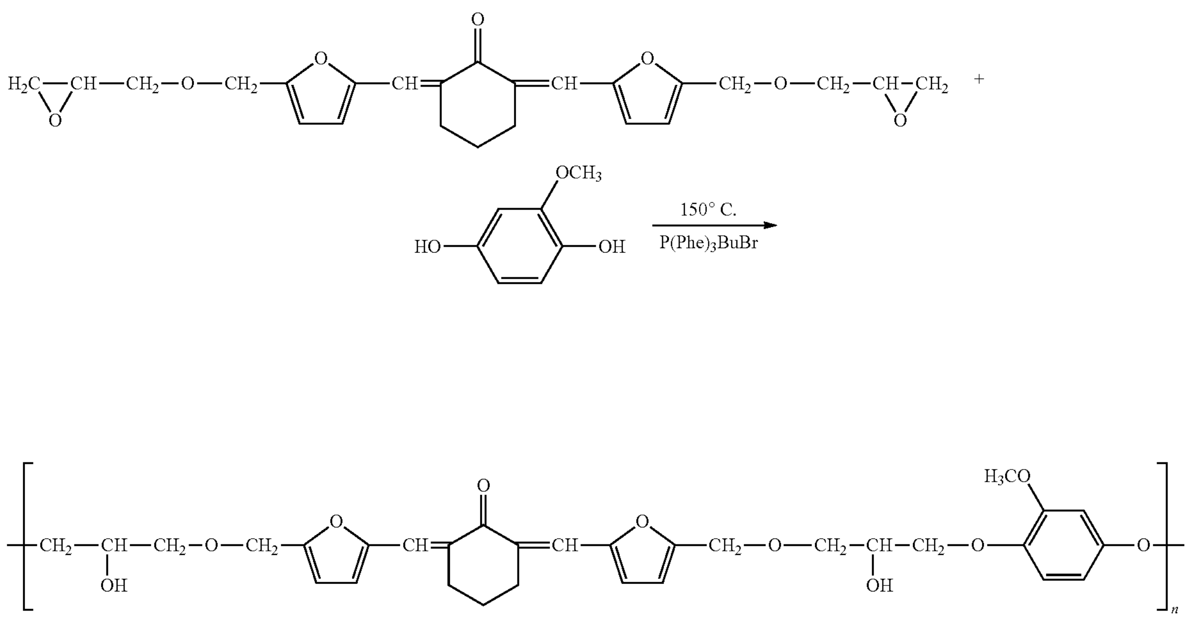

Figure 6:
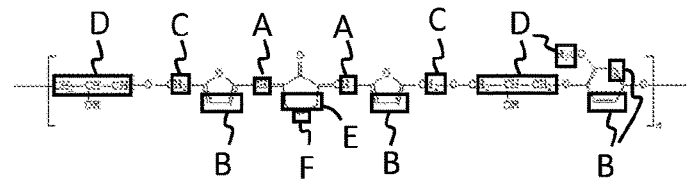
FIG. 6 is an NMR spectrum of the compound prepared in Example 6.
Figure 6:
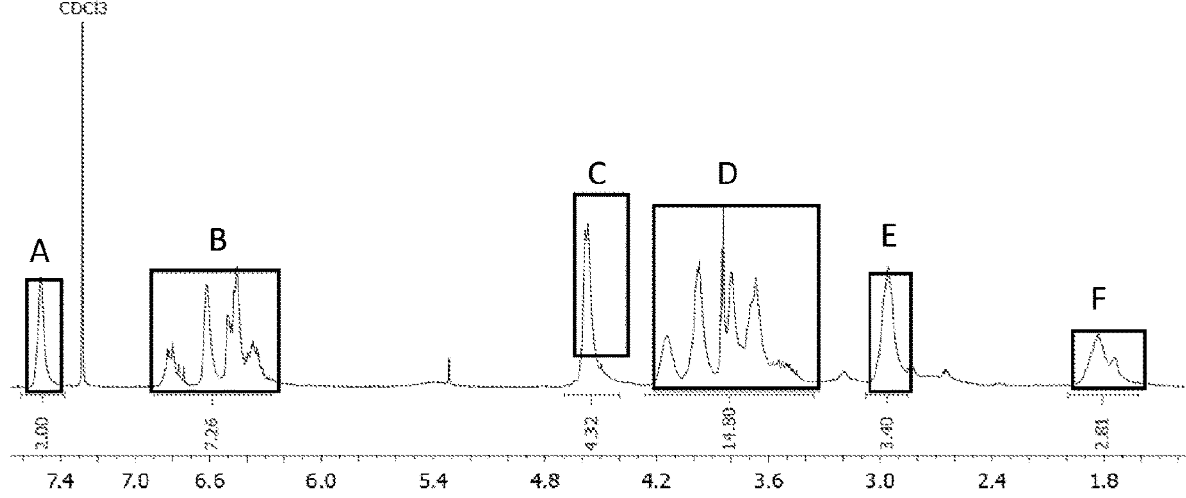

2 g (0.0047 mol) of the DGE and 0.66 g (0.0047 mol) of 2-methoxy hydroquinone were mixed in a glass vessel equipped with a condenser a stirrer and a temperature probe. The mixture was heated at 150° C. under argon flow until the mixture became homogeneous. 8 mg of butyl triphenyl phosphonium bromide was added and the mixture was maintained at 180° C. for two hours. The reaction product was observed in an NMR spectrum, showing the polyether is produced with a quantitative yield. The NMR spectrum is shown in FIG. 6.

Example 7

In Example 7, three polyether polymer samples were prepared from the vanillin-derived diphenol of Example 1A and the vanillin-derived diglycidyl ether of Example 1B, using the compounds shown in TABLE 1A.

TABLE 1A

| | Component | Amount (g) Sample 1 | Sample 2 | Sample 3 | Obtainable from |
|---|---|---|---|---|---|
| 1 | Tetramethyl bisphenol F diglycidyl ether | 45 | 0 | 0 | Laboratory made |
| 1 | Bis dimethyl phenol terpinolene diglycidyl ether | 0 | 0 | 50 | Laboratory made according to methods disclosed in WO 2018/125895 |
| 1 | Adduct of divanillin/ cyclohexanone and diglycidyl ether | 0 | 50 | 0 | Example 1B |
| 2 | Cardolite NX 2022 (cardanol) | 5 | 10 | 9 | Cardolite Corp. in Bristol, PA |
| 3 | Bis dimethyl phenol Terpinolene | 0 | 25.6 | 0 | Laboratory made according to methods disclosed in WO 2018/125895 |
| 3 | Adduct of divanillin and cyclohexanone | 30 | 0 | 20.4 | Example 1A |
| 4 | Cyclohexanone | 14.1 | 9.51 | 8.82 | |
| 5 | 1,5 Diazabicyclo(4,3,0) non - 5 ene (CAS 3001-72-7) | 0 | 0.16 | 0 | Sigma Aldrich |
| 5 | Ethyl triphenyl phosphonium | 0.08 | 0 | 0.16 | Sigma Aldrich |
| 6 | Cyclohexanone | 66 | 76.19 | 70.78 | Sigma Aldrich |
| | TOTAL (g) | 160.18 | 121.46 | 159.16 | |

The components for each sample were loaded in a glass vessel equipped with a temperature control system a stirrer, a total condenser, and nitrogen flow. First, components 1, 2, and 3 were mixed and homogenized, and heated progressively to 150° C. Component 4 was added, and the mixture was stirred at 150° C. until the mixture became clear. The temperature was allowed to fall to 140° C. before the addition of the catalyst (component 5). The temperature was maintained at 140° C. while checking the epoxy equivalent weight ("EEW") of the mixture regularly. When the EEW stabilized at approximately 2500-3000 (variation was less than 100 within 30 min), the mixture was cooled down and component 6 was added. Subsequently, the non-volatile content ("NVC"), EEW, and viscosity of the resulting polymers were evaluated as shown in TABLE 1B. EEW was measured using titration with perchloric acid (ASTM D1652). Viscosity was measured using a falling ball method at 25° C., where viscosity is determined as proportional to the time required for a calibrated stainless steel (SKF 4) 4 mm diameter ball to drop in the resin contained in a 20×300 mm glass tube. The viscosity of the resin in Poises is 6.56×t (in seconds), t being the time to fall 5 cm.

TABLE 1B

| | Sample 1 | Sample 2 | Sample 3 |
|---|---|---|---|
| NVC reaction | 85 | 90 | 90 |
| EEW | 2600 | 2900 | 2630 |
| Viscosity | 725 P | 153 P | 154 P |
| NVC measured 30 min at 180° C. | 50.30% | 51.60% | 51.90% |

Example 8

In Example 8, two coatings were prepared from the polyether polymers of Example 7 (Samples 2 and 3) using the compounds shown in TABLE 2A.

TABLE 2A

| Component | Amount (g) Sample 4 | Sample 5 | Obtainable from |
|---|---|---|---|
| Sample 2 polyether polymer at 50.2% NVC in cyclohexanone | 213.7 | | Example 7 |
| Sample 3 polyether polymer at 50.8% NVC in cyclohexanone | | 214 | Example 7 |
| Ethyldiglycol | 52.3 | 52.3 | Dow Chemical |
| Xylene | 52.3 | 52.3 | Exxon Chemie |
| Phenolic resin at 73% NVC in butanol, resole type | 35 | 35 | Hexion |

TABLE 2A-continued

| Component | Amount (g) Sample 4 | Sample 5 | Obtainable from |
|---|---|---|---|
| 85% $H_3PO_4$ at 10% in ethyldiglycol | 1.6 | 1.6 | Brenntag |
| Xylene | 46 | 46 | Exxon Chemical |
| Carnauba wax 18% | 6.5 | 6.5 | Munzing Chemie GmbH in Abstatt, Germany |
| TOTAL (g) | 407.4 | 407.7 | |

The polyether resin was loaded in a beaker and the ethyldiglycol and xylene were added. The mixture was stirred until homogenous. The phenolic resin was added while stirring, and the viscosity was adjusted with xylene. The wax was then added and the mixture was stirred for 20 min.

The coatings (Samples 4 and 5) were evaluated and compared to commercial samples. Each coating was applied on electrolytic tin plate ("ETP") panels with a bar coater (14—dry film weight: 5-6 g/m$^2$). The coatings were cured in a ventilated oven (12 min at 200° C. total oven time) and cooled for 8 h. The coated panels were tested and compared to commercial standards ("Std") of epoxy phenolic ("EP") and polyester phenolic ("PEP") coatings on regular food can ends. The results are shown in TABLE 2B below.

In the table, FW dry refers to dry film weight (what is left on the panel after curing). The size of each panel was A4 (210 mm×297 mm). Pinholes refer to microscopic holes in the varnish and is evaluated by visual comparison. The wedge bend was tested using a bend and impact tester Model 471 available from Erichsen GmbH in Hemer, Germany. Blush, adhesion, blistering, and corrosion were evaluated based on visual comparison. The values were obtained on regular food can ends before retorting or after retorting (1 hour at 130° C.) in water with 2% salt or in water with 3% acetic acid. A higher value indicates higher performance.

TABLE 2B

| | Std EP | Std PEP | Sample 4 | Sample 5 |
|---|---|---|---|---|
| Non-volatile content of coating compositions (30 minutes at 180° C.) | 41.5-43.5% | 42-44% | 31.50% | 33.10% |
| FW (dry) | 6.3 g | 8.4 g | 6 g | 6 g |
| Visual appearance | few pinholes | orange peel | pinholes orange peel | pinholes orange peel |
| Solvent Resistance Test (# of double rubs) | >100 | >100 | 85 | 110 |
| Wedge Bend Test | 82 | 83 | 74 | 77 |
| Metal Exposure Test before retort (in milliamps—"mA") | 0.9 | 0.4 | 2 | 2.5 |
| After retort in salt* | 8/0/10/10 | 8/0/10/10 | 9/10/10/10 | 8/9/10/10 |
| Metal Exposure Test after retort in salt (mA) | 6.1 | 3.3 | 7.5 | 9.1 |
| After retort in acetic acid* | 7/10/10/7/7 | 7/10/10/5/6 | 9/10/10/9/9 | 7/10/10/8/8 |
| Metal Exposure Test after retort in acetic acid (mA) | 3.8 | 1.3 | 7.2 | 16.1 |

*The values are in the order: blush/adhesion/blistering/corrosion.

It was observed that the experimental samples (Samples 4 and 5) performed at least as well as the commercial products. The enamel rater values are slightly higher due to the fact that the experimental samples do not contain wetting or flow additives.

Examples 9 and 10

The reactivity of the double bonds in a diepoxide depends on the structure of the monomer. An upgrade can be produced, for example, by heating the monomer at 140° C. for several hours (see, e.g., Example 2). The viscosity of the upgrade (e.g., described in Example 3, TABLE 1A) is not reduced by addition of free radical scavenger (TempoOH, CAS2226-96-2, available from Sigma Aldrich), which is an inhibitor of the reaction of double bonds. This demonstrates that the double bonds at 140° C. are not reactive. In some cases, the upgrade based on the diepoxide cannot be produced due to the too high reactivity of the double bonds (diepoxide of vanillin/acetone adduct).

Figure 7:
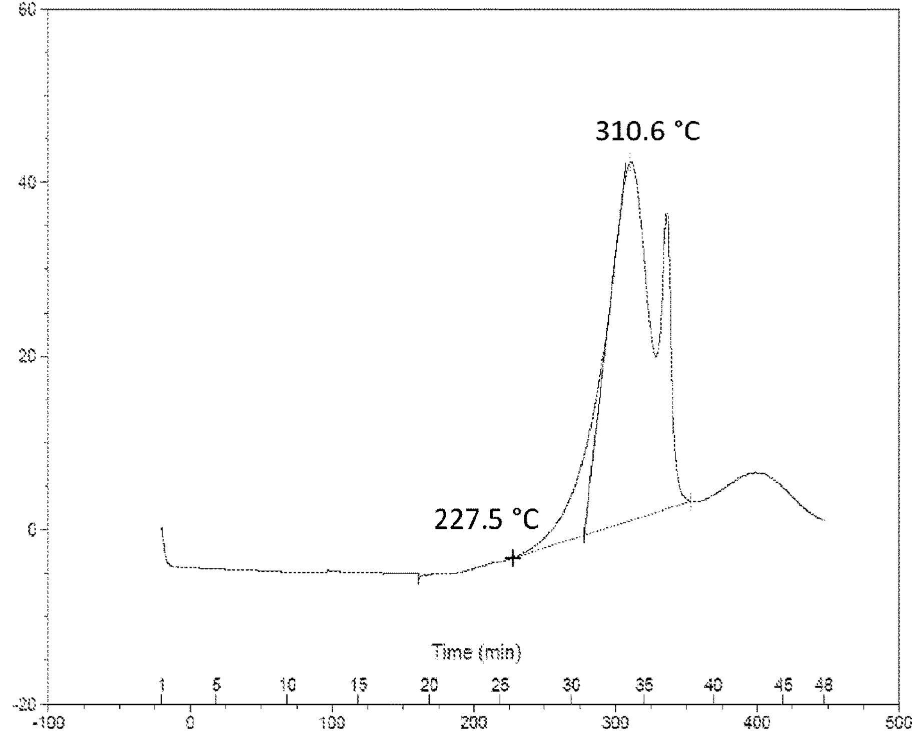
FIG. 7 is the DSC graph of the compound prepared in Example 9.

In Example 9, the stability of the diglycidyl ether of Example 4B (cyclohexanone 2,6 methylene bis (2-furan, 5-methanol glycidyl ether)) was tested using differential scanning calorimetry ("DSC"). The DSC graph is shown in FIG. 7. The compound was found to be stable up to 180° C.

Furthermore, a mixture of homopolymer and diepoxide monomer is obtained when the DGE of the adduct of vanillin and cyclohexanone (prepared in Example 1B) is reacted at 100° C. with styrene or methyl methacrylate in presence of benzyl peroxide.

In Example 10, the adduct of vanillin and cyclohexanone (prepared in Example 1A) and the DGE of the adduct of vanillin and cyclohexanone (prepared in Example 1B) were mixed with DMSO in the presence of benzoyl peroxide and heated to 100° C. to provide a crosslinked polymer upgrade. The mixture resulted in a gelled product. The produce could not be analyzed using NMR because of its insolubility. The product is represented by the following reaction:

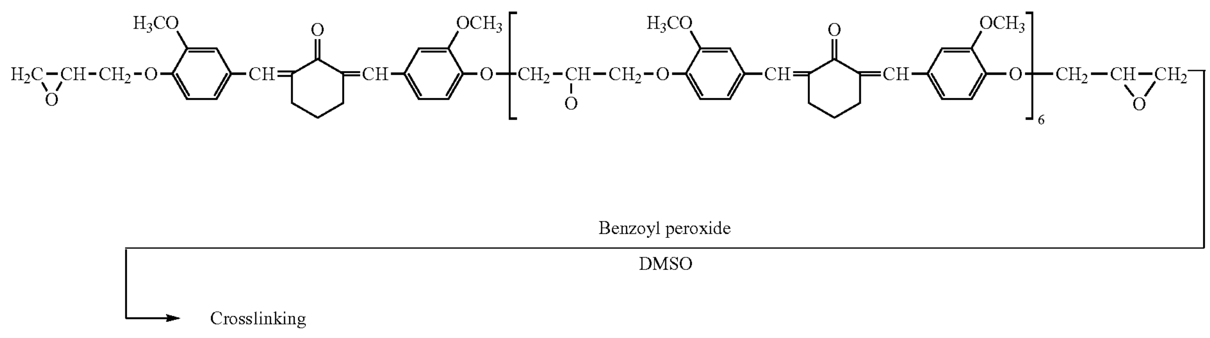

Without wishing to be bound by theory, the reactivity of the monomer towards a free radical is lower than styrene or usual acrylic monomers but an upgrade with an adequate free radical would react by hydrogen abstraction along the polyether backbone. The created radical could react with the double bond. This Hydrogen abstraction would allow the grafting of an acrylic portion, bringing water dispersibility thanks to the use of (meth)acrylic acid in the acrylic monomer mixture.

In the same manner, a free radical bearing an acid group could react by grafting or/and by addition on the double bond. As example, the upgrade was obtained by reaction of the adduct of vanillin and cyclohexanone (prepared in Example 1A) with the DGE of the adduct of vanillin and cyclohexanone (prepared in Example 1B) in presence of benzoyl peroxide and isobutyric acid.

All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. It should be understood that this disclosure is not intended to be unduly limited by the illustrative embodiments and examples set forth herein and that such examples and embodiments are presented by way of example only with the scope of the disclosure intended to be limited only by the claims set forth here.

The invention claimed is:

1. A polymer comprising one or more segments derived from a monomer of Formula (IIID) or a diepoxide thereof:

Formula (IIID)

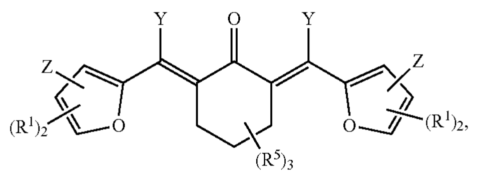

wherein each $R^1$ and Y are independently hydrogen or an organic group;

wherein each $R^5$ is independently selected from hydrogen or an organic group; and wherein Z is a group reactive with epichlorohydrin.

2. The polymer of claim 1, wherein the monomer of Formula-(HD) (IIID) constitutes 5 wt-% or more of the monomers used to make the polymer.

3. A coating or coating composition comprising the polymer of claim 1.

4. The coating composition of claim 3, wherein the coating composition comprises a food or beverage container coating composition that includes a solvent, and wherein the coating composition comprises from 10 wt-% to no greater than 50 wt-% of non-volatile components, and wherein the polymer:

has an Mn of at least 2,000;

a Tg of 30° C. or greater; and comprises 10 wt-% or more of the coating composition, based on total weight of resin solids in the coating composition.

5. The coating or coating composition of claim 4, formulated for application by inside spray coating or coil coating.

6. The coating or coating composition of claim 3, formulated for use on a food or beverage container comprising a metal substrate.

7. The coating or coating composition of claim 3, comprising a cured coating exhibiting a global extraction of less than about 50 parts-per-million (ppm) pursuant to the Global Extraction test.

8. The coating or coating composition of claim 3, comprising the polymer and a solvent, the coating composition comprising 10 wt-% or more of non-volatile components; and no greater than 50 wt-% of non-volatile components.

9. The coating or coating composition of claim 8, wherein the solvent comprises at least 50 wt-% of water.

10. The coating or coating composition of claim 3, wherein the coating composition is provided as a powder coating.

11. The polymer of claim 1, wherein the monomer of Formula (IIID) is represented by Formula (IIIE):

Formula (IIIE)

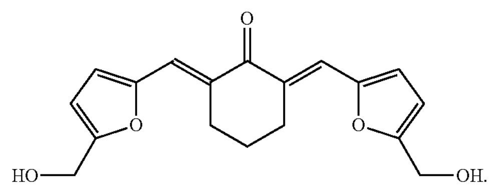

12. The polymer of claim 1, wherein the diepoxide of the monomer of Formula (IIID) is represented by Formula (IVC):

Formula (IVC)

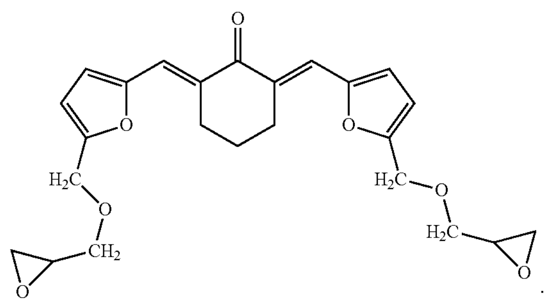

13. The polymer of claim 1, wherein the polymer comprises a polyether polymer.

14. The polymer of claim 1, wherein the polymer has a Tg of 50° C. or greater.

15. The polymer of claim 1, wherein the polymer has a number average molecular weight of 2000 or greater.

16. The polymer of claim 1, wherein the polymer includes one or more —$CH_2$—CH(OH)—$CH_2$— or —$CH_2$—$CH_2$—CH(OH)— backbone segments.

17. The polymer of claim 1, wherein the polymer has a polydispersity index (PDI) from about 1.5 to about 5.

18. The polymer of claim 1, wherein the polymer comprises a polyether-acrylate copolymer.

19. The polymer of claim 18, wherein one or more acrylic portions includes carboxylic acid groups and/or salt groups thereof.

20. The polymer of claim 1, wherein the polymer is free of structural units derived from bisphenol A, bisphenol F, or bisphenol S.

* * * * *